US009556249B2

(12) United States Patent
Jackson et al.

(10) Patent No.: US 9,556,249 B2
(45) Date of Patent: Jan. 31, 2017

(54) NEUREGULIN ANTAGONISTS AND USE THEREOF IN TREATING CANCER

(75) Inventors: Erica Jackson, San Francisco, CA (US); Eric Alejandro Sweet-Cordero, San Francisco, CA (US)

(73) Assignees: Genentech, Inc., South San Francisco, CA (US); The Board of Trustees of the Leland Stanford Junior University, Palo Alto, CA (US)

( * ) Notice: Subject to any disclaimer, the term of this patent is extended or adjusted under 35 U.S.C. 154(b) by 799 days.

(21) Appl. No.: 13/029,199

(22) Filed: Feb. 17, 2011

(65) Prior Publication Data

US 2011/0229493 A1 Sep. 22, 2011

Related U.S. Application Data

(60) Provisional application No. 61/305,878, filed on Feb. 18, 2010.

(51) Int. Cl.

| *A61K 39/395* | (2006.01) |
|---|---|
| *C07K 14/475* | (2006.01) |
| *A61K 31/7088* | (2006.01) |
| *A61K 45/06* | (2006.01) |
| *C07K 14/71* | (2006.01) |
| *C12N 15/113* | (2010.01) |
| *C07K 16/22* | (2006.01) |
| *A61K 38/00* | (2006.01) |

(52) U.S. Cl.
CPC ....... *C07K 14/4756* (2013.01); *A61K 31/7088* (2013.01); *A61K 39/3955* (2013.01); *A61K 45/06* (2013.01); *C07K 14/71* (2013.01); *C12N 15/1136* (2013.01); *A61K 38/00* (2013.01); *C07K 2319/30* (2013.01); *C12N 2310/14* (2013.01); *C12N 2310/531* (2013.01)

(58) Field of Classification Search
CPC ........ A61K 39/395; C07K 16/22; C07K 16/26
See application file for complete search history.

(56) References Cited

U.S. PATENT DOCUMENTS

| 6,696,290 B2 * | 2/2004 | Fitzpatrick ......... C07K 14/4705 435/252.3 |
| 7,449,184 B2 * | 11/2008 | Allison ................... C07K 16/32 424/130.1 |
| 2007/0036797 A1 * | 2/2007 | Kim ....................... C07K 16/22 424/155.1 |

FOREIGN PATENT DOCUMENTS

| EP | 2 009 114 A1 | 12/2008 |
| WO | 2006/017184 A2 | 2/2006 |

OTHER PUBLICATIONS

Romond, E.H., et al. The New England Journal of Medicine, 353(16): 1673-1684.*
Decatris, M.P., et al. Cancer Treatment Reviews, 4: 53-81, 2004.*
Agus et al., "Targeting ligand-activated ErbB2 signaling inhibits breast and prostate tumor growth" Cancer Cell 2(2):127-137 (Aug. 2002).
Al Moustafa et al., "Expression of P185erbB-2, P160erbB-3, P180erb-4, and Heregulin Alpha in Human Normal Bronchial Epithelial and Lung Cancer Cell Lines" Anticancer Research 19:481-186 (1999).
Baldi and Long et al., "A Bayesian framework for the analysis of microarray expression data: regularized t-test and statistical inferences of gene changes" Method Biochem Anal 17(6):509-519 (2001).
Bao et al., "Stem cell-like glioma cells promote tumor angiogenesis through vascular endothelial growth factor." Cancer Research 66(16):7843-7848 (Aug. 15, 2003).
Brennan et al., "Cancer stem cells: controversies in multiple myeloma" Journal of molecular medicine 87:1079-1085 (2009).
Breuleux, "Role of heregulin in human cancer" Cell Mol Life Sci 64:2358-2377 (2007).
Carey et al., "Kinetic Analysis of Epidermal Growth Factor Receptor Somatic Mutant Proteins Shows Increased Sensitivity to the Epidermal Growth Factor Receptor Tyrosine Kinase Inhibitor, Erlotinib" Cancer Research 66:8163-8171 (2006).
Costello et al., "Human acute myeloid leukemia CD34+/CD38−progenitor cells have decreased sensitivity to chemotherapy and Fas-induced apoptosis, reduced immunogenicity, and impaired dendritic cell transformation capacities." Cancer Research 60(16):4403-4411 (Aug. 15, 2000).
Dahabreh et al., "Somatic EGFR Mutation and Gene Copy Gain as Predictive Biomarkers for Response to Tyrosine Kinase Inhibitors in Non-Small Cell Lung Cancer" Clinical Cancer Research 16:291-303 (Dec. 22, 2009).
Dean et al., "Tumor Stem Cells and Drug Resistance" Nature Reviews 5:275-284 (Apr. 2005).
Ding et al., "Somatic Mutations Affect Key Pathways in Lung Adenocarcinoma" Nature 455(23):1069-1075 (Oct. 2008).
Doebele et al., "New strategies to overcome limitations of reversible EGFR tyrosine kinase inhibitor therapy in non-small cell lung cancer" Lung Cancer 61:1-12 (2010).
Dylla et al., "Colorectal Cancer Stem Cells are Enriched in Xenogeneic Tumors" PloS one 3(6):1-13 (Jun. 2008).
Goffin et al., "First-line Systemic Chemotherapy in the Treatment of Advanced Non-small Cell Lung Cancer: A Systematic Review" Journal of Thoracic Oncology 5:260-274 (2010).
Gollamudi et al., "Autocrine activation of ErbB2-ErbB3 receptor complex by NRG-1 in non-small cell lung cancer cell lines" Lung Cancer 43:135-143 (2004).
Gray et al., "pHUSH: a single vector system for conditional gene expression" BMC Biotechnol 7:61 (Sep. 26, 2007).
Hirsch et al., "Combination of EGFR gene copy numer and protein expression predicts outcome for advanced non-small-cell lung cancer patients treated with gefitinib" Annals of Oncology 18:752-760 ( 2007).
Holmes et al., "Idenification of Heregulin, A Specific Activator of p185 $^{erbB2}$" Science 256:1205-1210 (May 22, 1992).
Horner et al., "SEER Cancer Statistics Review" National Cancer Institute:1-110 (1975-2006).

(Continued)

*Primary Examiner* — Misook Yu
*Assistant Examiner* — Anne Holleran

(57) ABSTRACT

The invention provides neuregulin antagonists and methods of using the neuregulin antagonists in delaying the time to tumor recurrence or preventing resistance of cancer cells to treatment with a therapeutic agent.

15 Claims, 11 Drawing Sheets

(56) References Cited

OTHER PUBLICATIONS

Hsieh et al., "Neuregulin/Erythroblastic Leukemia Viral Oncogene Homolog 3 Autocrine Loop Contributes to Invasion and Early Recurrence of Human Hepatoma" Hepatology 53(2):504-516 (Jan. 18, 2011).
Jackson et al., "Analysis of lung tumor initiation and progression using conditional expression of oncogenic K-ras" Genes & Development 15:3243-3248 (Oct. 4, 2001).
Johnson et al., "Rationale for a Phase II Trial of Pertuzumab, a HER-2 Dimerization Inhibitor, in Patients with Non-Small Cell Lung Cancer" Clinical Cancer Research 12:4436s-4440s (May 22, 2006).
Junttila et al., "Ligand-Independent HER2/HER3/PI3K Complex Is Disrupted by Trastuzumab and Is Effectively Inhibited by the PI3K Inhibitor GDC-0941" Cancer Cell 15:429-440 (May 5, 2009).
Kosaka et al., "Mutations of the Epidermal Growth Factor Receptor Gene in Lung Cancer Biological and Clinical Implications" Cancer Research 64:8919-8923 (2004).
Kuyama et al., "Impact of HER2 Gene and Protein Status on the Treastment Outcome of Cisplatin-Based Chemoradiotherapy for Locally Advanced Non-small Cell Lung Cancer" Journal of Thoracic Oncology 3:477-482 (2008).
Li et al., "Development of an Autocrine Neuregulin Signaling Lopp with Malignant Transformation of Human Breast Epithelial Cells" Cancer Research 64:7078-7085 (2004).
Liu et al., "AKT1 Amplification Regulates Cisplatin Resistance in Human Lung Cancer Cells through the Mammalian Target of Rapamycin/p70S6K1" Cancer Research 67:6325-6332 (2007).
:Lung Cancer Principles and Practice 3 edition, Philadelphia:Lippincott Williams & Wilkins, (2005).
Lynch et al., "Activating Mutations in the Epidermal Growth Factor Receptor Underlying Responsiveness of Non-Small-Cell Lung Cancer to Gefitinib" New Engl J Med 350(21):2129-2139 (May 20, 2004).
Marchetti et al., "EGFR Mutations in Non-SMall-Cell Lung Cancer: Analysis of a Large Series of Cases and Development of a Rapid and Sensitive Method for Diagnostic Screening With Potential Implications on Pharmacologic Treatment" Journal of Clinical Oncology 23:857-865 (Feb. 1, 2005).
Matsui et al., "Characterization of clonogenic multiple myeloma cells" blood 103:2332-2336 (2004).
Menendez et al., "Transphosphorylation of kinase-dead HER3 and breast cancer progression: a new standpoint of an old concept revisited?" Breast Cancer Research 9(5):1-5 (Oct. 19, 2007).
Menendez et al., "Trastuzumab in Combination With Heregulin-Activated Her-2 (erB-2) Triggers a Receptor-Enhanced Chemosensitivity Effect in the Absence of Her-2 Overexpression" Journal of Clinical Oncology 24(23):3735-3746 (Aug. 10, 2006).
Novak et al., "Z/EG, a Double Reporter Mouse Line the Expresses Enhanced Green Fluorescent Protein Upon Cre-Mediated Excision" Genesis 28(3-4):147-155 (Nov. 16, 2000).
Oliver et al., "Chronic cisplatin treatment promotes enhanced damage repair and tummor progression in a mouse model of lung cancer" Genesis & Development 24 (2010).
Paez et al., "EGFR Mutations in Lung Cancer: Correlation with Clinical Response to Gefitinib Therapy" Science 304:1497-1500 (Jun. 4, 2004).
Pao et al., "Acquired Resistance of Lung Adenocarcinomas to Gefitinib or Erlotinib is Associated with a Second Mutation in the EGFR Kinase Domain" PLoS Medicine 2(3):0225-0235 (Mar. 2005).
Patel et al., "Neuregulin-1 and human epidermal growth factor receptors 2 and 3 play a role in human lung development in vitro" Am J Respir Cell Mol Biol. 22(4):432-440 (2000).
PCT International Search Report for PCT/US2011/025163, pp. 1-6 (Date of mailing of the international search report Jun. 17, 2011).
Phillips et al., "The response of CD24(-/low)/CD44+ breast cancer-initiating cells to radiation." Journal of the National Cancer Institute 98(24):1777-1785 (Dec. 20, 2006).
Reissmann et al., "Amplification and overexpression of the cyclin D1 and epidermal growth factor receptor genes in non-small lung cancer" Lung Cancer Study Group 125:61-70 (1999).
Sarup et al., "Human epidermal growth factor receptor (HER-1:HER=3) Fc-mediated heterodimer has braod antiproliferative activity in vitro and in human tumor xenografts" Molecular Cancer Therapeutics 7(10):3223-3236 (Oct. 2008).
Schaefer et al., "γ-Heregulin: A novel heregulin isoform that is an autocrine growth factor for the human breast cancer cell line, MDA-MB-175" Oncogene 15:1385-1394 (1997).
Sheng, Q. et al., "An Activated ErbB3/NRG1 Autocrine Loop Supports In Vivo Proliferation in Ovarian Cancer Cells" Cancer Cell 17:298-310 (Mar. 2010).
Shi et al., "Overexpression of the c-erbB-2/neu-encoded p185 protein in primary lung cancer" Molecular Carcinogenesis 5:213-218 (1992).
Shigematsu et al., "Clinical and Biological Features Associated With Epidermal Growth Factor Receptor Gene Mutations in Lung Cancers" Journal of the National Cancer Institute 97(5):339-346 (Mar. 2, 2005).
Singh et al., "Assessing therapeutic responses in Kras mutant cancers using genetically engineered mouse models" Nature Biotechnology 28(6):585-593 (Jun. 2010).
Sinnberg et al., "Inhibition of PI3K-AKT-mTOR signaling sensitizes melanoma cells to cisplatin and temozolomide" Journal of Investagative Dermatology 129:1500-1515 (2009).
Sithanandam et al., "The ERBB3 receptor in cancer and cancer gene therapy" Gene Therapy 15(7):413-448 (Apr. 11, 2008).
Storey et al., "Statistical significance for genomewide studies" Proc Natl Acad Sci USA 100(16):9440-9445 (Aug. 5, 2003).
Tsai et al., "Blockage of heregulin expression inhibits tumorigenicity and metastasis of breast cancer" Oncogene 22(5):761-768 (Feb. 6, 2003).
Tzahar et al., "ErbB-3 and ErbB-4 function as the respective low and high affinity receptors of all Neu differentiation factor/herefulin isoforms" Journal of Biological Chemistry 269(40):25226-25233 (Oct. 7, 1994).
Villeneuve et al., "cDNA microarray analysis of isogenic paclitaxel and doxorubicin-resistant breast tumor cell lines reveals distinct drug-specific genetic signatures of resistance" Breast Cancer Research and Treatment 96(1):17-39 (Mar. 1, 2006).
Weiner et al., "Expression of the neu Gene-encoded Protein (P185$^{neu}$) in Human Non-Small Cell Carcinomas of the Lung" Cancer Res 50(2):421-425 (Jan. 15, 1990).
Yarden, "Biochemical Analysis of the Ligand for the neu Oncogenic Receptor" Biochemistry—US 30:3543-3550 (1991).
Yuste et al., "Activation of ErbB2 by overexpression or by transmembrane neuregulin results in differential signaling and sensitivity to herceptin" Cancer Research 65:6801-6810 (2005).
Zhou et al., "Targeting ADAM-mediated ligand cleavage to inhibit HER3 and EGFR pathways in non-small cell lung cancer" Cancer Cell 10(1):39-50 (Jan. 1, 2006).
Puricelli et al., "Heregulin inhibits proliferation via ERKs and phosphatidyl-inositol 3-kinase activation but regulates urokinase plasminogen activator independently of these pathways in metastatic mammary tumor cells" Int. J. Cancer 100:642-653 (2002).

* cited by examiner

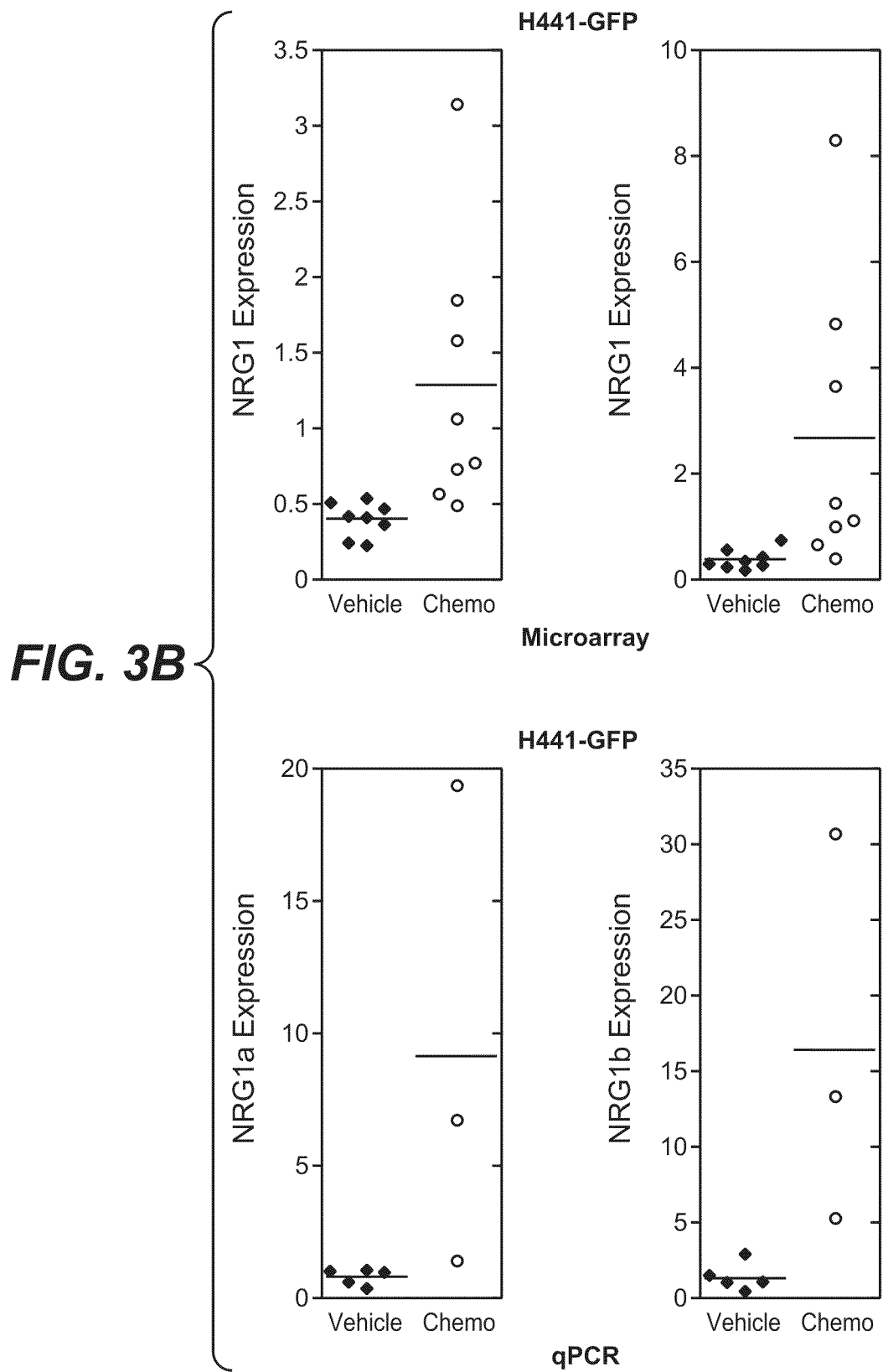

```
                         SEQUENCE LISTING

<160> NUMBER OF SEQ ID NOS: 10

<210> SEQ ID NO 1
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 1
gatcccccat ggtgaacata gcgaatttca agagaattcg ctatgttcac catgtttttt     60
ggaaa                                                                 65

<210> SEQ ID NO 2
<211> LENGTH: 65
<212> TYPE: DNA
<213> ORGANISM: Artificial sequence
<220> FEATURE:
<223> OTHER INFORMATION: synthetic oligonucleotide

<400> SEQUENCE: 2
agcttttcca aaaaacatgg tgaacatagc gaattctctt gaaattcgct atgttcacca     60 tggg g                                                                65

<210> SEQ ID NO 3
<211> LENGTH: 65
<212> TYPE: DNA
<213> ORGANISM: Artificial sequence
<220> FEATURE:
<223> OTHER INFORMATION: synthetic oligonucleotide

<400> SEQUENCE: 3
gatccccgag tatatgtgca aagtgattca agagatcact ttgcacatat actctttttt     60
```

```
ggaaa                                                               65

<210> SEQ ID NO 4
<211> LENGTH: 65
<212> TYPE: DNA
<213> ORGANISM: Artificial sequence
<220> FEATURE:
<223> OTHER INFORMATION: synthetic oligonucleotide

<400> SEQUENCE: 4
agcttttcca aaaagagta tatgtgcaaa gtgatctctt gaatcacttt gcacatatac    60
tcggg                                                               65

<210> SEQ ID NO 5
<211> LENGTH: 65
<212> TYPE: DNA
<213> ORGANISM: Artificial sequence
<220> FEATURE:
<223> OTHER INFORMATION: synthetic oligonucleotide

<400> SEQUENCE: 5
gatccccgat cacaactgct gcttaattca agagattaag cagcagttgt gatctttttt    60
ggaaa                                                               65

<210> SEQ ID NO 6
<211> LENGTH: 65
<212> TYPE: DNA
<213> ORGANISM: Artificial sequence
<220> FEATURE:
<223> OTHER INFORMATION: synthetic oligonucleotide

<400> SEQUENCE: 6
agcttttcca aaaagatca caactgctgc ttaatctctt gaattaagca gcagttgtga    60
tcggg                                                               65

<210> SEQ ID NO 7
<211> LENGTH: 65
<212> TYPE: DNA
<213> ORGANISM: Artificial sequence
<220> FEATURE:
<223> OTHER INFORMATION: synthetic oligonucleotide

<400> SEQUENCE: 7
gatccccaag aggatgtcaa cggttattca agagataacc gttgacatcc tcttttttt    60 ggaaa                                                               65

<210> SEQ ID NO 8
<211> LENGTH: 65
<212> TYPE: DNA
<213> ORGANISM: Artificial sequence
<220> FEATURE:
<223> OTHER INFORMATION: synthetic oligonucleotide

<400> SEQUENCE: 8
agcttttcca aaaaaagag gatgtcaacg gttatctctt gaataaccgt tgacatcctc    60
ttggg                                                               65

<210> SEQ ID NO 9
<211> LENGTH: 65
<212> TYPE: DNA
<213> ORGANISM: Artificial Sequence
<220> FEATURE:
```

```
<223> OTHER INFORMATION: synthetic oligonucleotide

<400> SEQUENCE: 9
gatcccccat ggtgaacata gcgaatttca agagaattcg ctatgttcac catgtttttt    60
ggaaa                                                                65

<210> SEQ ID NO 10
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 10
agcttttcca aaaacatggt gaacatagc gaattctctt gaaattcgct atgttcacca    60
tgggg                                                                65
```

NEUREGULIN ANTAGONISTS AND USE THEREOF IN TREATING CANCER

CROSS REFERENCE TO RELATED APPLICATIONS

This application claims the benefit of U.S. Provisional Application No. 61/305,878, filed Feb. 18, 2010, the disclosure of which is incorporated herein by reference in its entirety.

FIELD OF THE INVENTION

The present invention relates to the treatment of cancer with neuregulin antagonists.

BACKGROUND

The identity and properties of cancer stem cells (CSCs) has been a field of intense study in recent years. Evidence is accumulating that tumors are a heterogeneous mixture of cells with different biological properties. The isolation of distinct cell populations with the unique ability to initiate tumor growth has been reported for numerous hematologic malignancies and solid tumors. However, inconsistencies have emerged in the use of specific cell surface markers to prospectively identify CSCs. For example, disparate findings on stem cell phenotype have been reported for leukemias, pancreatic, colorectal, brain and breast cancers (Reviewed in Brennan and Matsui 2009). Furthermore, estimates of CSC frequency vary dramatically between tumor types and patients. The role of CSCs in maintaining the growth of an established tumor or in re-initiating a tumor after chemotherapy either at a primary or distant site, remains to be determined.

For most cancer patients, disease relapse after chemotherapy is a major cause of mortality. Accordingly, a better understanding of the tumor re-initiating cells (TRICs) responsible for relapse is needed in order to better treat patients who have experienced a recurrence of cancer after initially responding to chemotherapeutic treatment. This is particularly relevant for non-small cell lung cancer (NSCLC) because more than two thirds of NSCLC patients are not candidates for surgical resection. Most patients present with advanced disease and are treated with chemotherapy, radiation or a combination of the two (lung cancer principles and practice). However, the 5 year survival rate for locally advanced disease remains at 23.7% and at 3.5% for advanced disease despite good initial responses to therapy (Horner et al. SEER).

Deregulation of EGFR signaling via overexpression or activating mutations has been shown to be a frequent event in NSCLC (reviewed in Dahabreh et al., 2010). EGFR is the prototypical member of the HER family of tyrosine kinases, which includes EGFR (Her1), Her2, Her3 and Her4. Her2 lacks a functional ligand binding domain (Graus-Porta 1997) and Her3 lacks tyrosine kinase activity (Guy 1994), so these receptors must act as heterodimers. Recent evidence shows that other Her family members may also play a role in NSCLC. However their contributions to the disease are less well characterized and studies have often focused on their interactions with EGFR activation (Kuyama et al. 2008, Hirsch 2009, Zhou 2006, Johnson 2006, Ding 2008).

Neuregulin is a ligand for the Her3 and Her4 receptor tyrosine kinases. There are four known members of the neuregulin family, NRG1, NRG2, NRG3, and NRG4 (Falls 2003). The NRG1 transcript undergoes extensive alternative splicing resulting in at least 15 different isoforms. All active isoforms share an EGF-like domain that is necessary and sufficient for activity (Holmes 1992, Yarden 1991). NRG1 autocrine signaling has been shown to regulate lung epithelial cell proliferation (Jinbo 2002) and to play a role in human lung development (Patel 2000) and has been implicated in insensitivity of NSCLC to EGFR inhibitors (Zhou 2006).

The need exists to provide therapeutics effective in treating resistant cancers and patients who have experienced a recurrence of cancer.

SUMMARY

One aspect of the invention provides for a method of increasing time to tumor recurrence in a cancer patient comprising administering to the patient an effective amount of a neuregulin antagonist. In one embodiment, the method further comprises administering a therapeutic agent to the patient. In one embodiment, the therapeutic agent is a chemotherapeutic agent or an antibody. In certain embodiments the chemotherapeutic agent is paclitaxal or cisplatin or a combination of paclitaxal and cisplatin.

In certain embodiments the antibody is an EGFR, HER2, HER3, or HER4 antibody. In certain embodiments, the cancer the patient is suffering from is non-small cell lung cancer, breast cancer, ovarian cancer, head and neck cancer, cervical cancer, bladder cancer, oesophageal cancer, prostate cancer, or colorectal cancer.

In one embodiment, the increase in time to tumor recurrence is at least 1.25 fold greater than the time to recurrence in the absence of the neuregulin antagonist. In one embodiment, the increase in time to tumor recurrence is at least 1.50 fold greater than the time to recurrence in the absence of the neuregulin antagonist.

In certain embodiments, the neuregulin antagonist is an antibody, a small molecule, an immunoadhesin, or an RNA. In one embodiment, the neuregulin antagonist is a NRG1 antagonist. In one embodiment, the NRG antagonist is an anti-NRG1 antibody.

BRIEF DESCRIPTION OF THE DRAWINGS

FIG. 3B. Enrichment of NRG1 mRNA in TRICs in the H441 xenograft model shown by two different microarray probes. This was validated by qPCR for NRG1a and NRG1b using RNA from the same tumor samples used for microarray analysis.

DETAILED DESCRIPTION OF EMBODIMENTS OF THE INVENTION

I. Definitions

Figure 1:
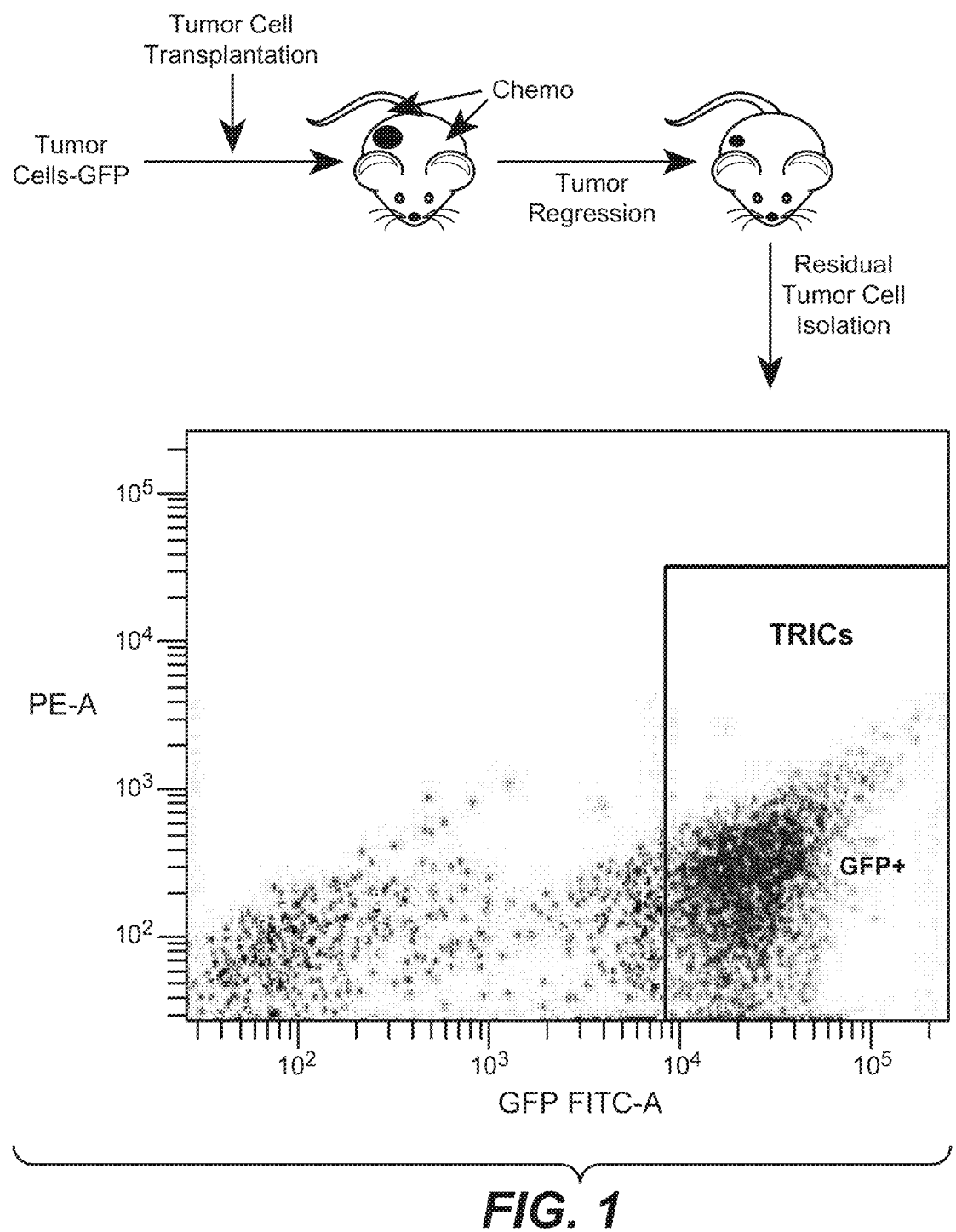
FIG. 1. Schematic representation of an in vivo model for studying tumor re-initiating cells (TRICs).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-NRG antibody" and "an antibody that binds to NRG" refer to an antibody that is capable of binding NRG with sufficient affinity such that the antibody is useful as a diagnostic and/or therapeutic agent in targeting NRG. In one embodiment, the extent of binding of an anti-NRG antibody to an unrelated, non-NRG protein is less than about 10% of the binding of the antibody to NRG as measured, e.g., by a radioimmunoassay (RIA). In certain embodiments, an antibody that binds to NRG has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-NRG antibody binds to an epitope of NRG that is conserved among NRG from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bii^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" or "patient" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual, subject, or patient is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-NRG antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N— to C-terminus, each heavy chain has a variable region (VH), also called a variable heavy domain or a heavy chain variable domain, followed by three constant domains (CH1, CH2, and CH3). Similarly, from N— to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "NRG" as used herein, refers to any native neuregulin (also known as heregulin) from any vertebrate source, including mammals such as primates (e.g. humans) and rodents (e.g., mice and rats), unless otherwise indicated. The term encompasses "full-length," unprocessed NRG as well as any form of NRG that results from processing in the cell. The term also encompasses naturally occurring variants of NRG, e.g., splice variants or allelic variants. There are four known forms of NRG: NRG1 (Holmes, W. E. et al., Science 256:1205-1210 (1992)); NRG2 (Caraway, K. L. et al., Nature 387:512-516 (1997)); NRG3 (Zhang, E. et al., Proc Natl Acad Sci USA 94:9562-9567)); and NRG4 (Haran, D. et al., Oncogene 18:2681-2689)). Due to alternative splicing there are two active isoforms of the NRG1 EGF-like domain that is required for receptor binding, referred to as NRG1 alpha (NRG1α) and NRG1beta (NRGβ). Sequences of exemplary human NRGIs are shown in Genbank Accession No. BK000383 (Falls, D. L., Ex Cell Res, 284:14-30 (2003) and in U.S. Pat. No. 5,367,060.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the NRG antagonists of the invention are used to delay development of a disease, slow the progression of a disease, prevent relapse, or to increase time to tumor recurrence. In certain embodiments, treatment results in a reduction in the number of or complete absence of tumor reinitiating cells; a decrease in number of tumor reinitiating cells in a solid tumor relative to cells in the tumor that are not tumor reinitiating cells; and/or inhibition of the proliferation of tumor reinitiating cells. In certain embodiments, treatment with a NRG antagonist results in an increase in time to tumor recurrence of at least 1.25, 1.50, 1.75, 2.0 fold greater than the time to tumor recurrence in the absence of treatment with an NRG antagonist.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

The present invention is based on the finding that NRG autocrine signaling plays an important role in the survival and proliferation of a small population of tumor cells after chemotherapy in an otherwise chemosensitive tumor. These surviving tumor cells, referred to herein as "tumor reinitiating cells", or "TRICs", are responsible for the relapse and recurrence of cancer in patients whose cancer previously was treated with a therapeutic agent. In one embodiment, the therapeutic agent used to treat the patient is a chemotherapeutic agent. In another embodiment, the therapeutic agent used to treat the patient is an antigen binding agent, such as an antibody, or fragment thereof.

Inhibition of NRG signaling results in the delay or prevention of tumor relapse or recurrence after treatment with a therapeutic agent. Accordingly, one aspect of the invention provides for NRG antagonists that inhibit NRG induced signaling. In one embodiment, the NRG antagonist is an NRG1 antagonist. NRG antagonists find use in treating cancer and in preventing resistance and/or recurrence of cancer after treatment with a therapeutic agent. Another aspect of the invention provides for a method of preventing resistance to treatment with a therapeutic agent in a patient by administering to the patient a NRG antagonist. Another aspect of the invention provides for preventing recurrence of cancer after treatment with a therapeutic agent by administering to the patient a NRG antagonist. Yet another aspect of the invention provides for a model characterizing TRICs. As described in the Examples and accompanying Figures, this model comprises cells that show a robust response to treatment resulting in significant tumor regression followed by disease relapse after the cessation of the treatment. The model finds use in screening for compounds that can be used to target the TRICs and for determining the molecular basis for the TRICs.

Specific aspects include a method of preventing tumor recurrence or increasing time to tumor recurrence comprising administering to the patient an effective amount of a NRG antagonist. In one embodiment, the patient has been treated with a therapeutic agent, such as a chemotherapeutic agent or an antigen binding agent, such as an antibody. In one embodiment, the cancer comprises tumor reinitiating cells. In one embodiment, the cancer is non-small cell lung cancer. In one embodiment, the cancer is breast cancer. In one embodiment, the patient was treated with a chemotherapeutic agent. In one embodiment, the chemotherapeutic agent is an agent used as a standard of care treatment for cancer. In one embodiment, the chemotherapeutic agent is paclitaxal or cisplatin or a combination of paclitaxal and cisplatin. In one embodiment, the chemotherapeutic agent is not a tyrosine kinase inhibitor. In another embodiment, the chemotherapeutic agent is a tyrosine kinase inhibitor. In one embodiment, the chemotherapeutic agent is an inhibitor EGFR, HER2, HER3 and/or HER4. Another embodiment comprises additionally administering a chemotherapeutic agent to the patient in combination with a NRG antagonist.

In another embodiment, the patient was treated with an antibody. In one embodiment, the antibody is an anti-tyrosine kinase antibody. In one embodiment, the antibody is an EGFR, HER2, HER3 and/or HER4 antibody. Another embodiment comprises additionally administering an antibody to the patient in combination with a NRG antagonist.

In certain embodiments, the time to tumor recurrence is at least 1.25, 1.50, 1.75, 2.0, 2.5, 5.0, 10, 20, or 50 times greater than the time to tumor recurrence in the absence of the neuregulin antagonist.

Another aspect provides for a method of treating a patient with a resistant cancer comprising administering to a patient an effective amount of a NRG antagonist. In one embodiment, the cancer comprises tumor reinitiating cells. In one embodiment, the cancer is non-small cell lung cancer. In one embodiment, the cancer is breast cancer. In one embodiment, the cancer is resistant to treatment with chemotherapeutic agents. In one embodiment, the cancer is resistant to treatment with paclitaxal or cisplatin or a combination of paclitaxal and cisplatin. In one embodiment, the cancer is resistant to treatment with a tyrosine kinase inhibitor. In one embodiment, the cancer is resistant to treatment with an EGFR, HER2, HER3 and/or HER4 inhibitor. Another embodiment comprises additionally administering a chemotherapeutic agent to the patient. In one embodiment, the chemotherapeutic agent is paclitaxal or cisplatin or a combination of paclitaxal and cisplatin. In one embodiment, the chemotherapeutic agent is an EGFR, HER2, HER3 and/or HER4 inhibitor.

In one embodiment, the cancer is resistant to treatment with a therapeutic antibody. In one embodiment, the cancer is resistant to treatment with an EGFR, HER2, HER3, or HER4 antibody. Another embodiment comprises additionally administering an antibody to the patient. In one embodiment, the antibody is trastuzumab or pertuzumab.

Another aspect provides for a method of preventing resistance in a cancer comprising administering to a patient who has cancer an effective amount of a NRG antagonist and a therapeutic agent. In one embodiment, the cancer comprises tumor reinitiating cells. In one embodiment, the cancer is non-small cell lung cancer. In one embodiment, the cancer is breast cancer. In one embodiment, the cancer is resistant to treatment with chemotherapeutic agents. In one embodiment, the cancer resistant to treatment with paclitaxal or cisplatin or a combination of paclitaxal and cisplatin. In one embodiment, the chemotherapeutic agent is not a tyrosine kinase inhibitor. In another embodiment, the chemotherapeutic agent is a tyrosine kinase inhibitor. In one embodiment, the chemotherapeutic agent is an inhibitor EGFR, HER2, HER3 and/or HER4. Another embodiment comprises additionally administering a chemotherapeutic agent to the patient. In one embodiment, the chemotherapeutic agent is paclitaxal or cisplatin or a combination of paclitaxal and cisplatin.

In one embodiment, the cancer is resistant to treatment with a therapeutic antibody. In one embodiment, the cancer is resistant to treatment with an EGFR, HER2, HER3, or HER4 antibody. Another embodiment comprises additionally administering an antibody to the patient. In one embodiment, the antibody is trastuzumab or pertuzumab.

In these methods of therapeutic use, the NRG antagonist is an antibody, a small molecule, an immunoadhesin, or an RNA. In one embodiment, the NRG antagonist is a NRG1 antagonist. In one embodiment, the NRG antagonist is an anti-NRG1 antibody.

In a further aspect, the invention provides for the use of a neuregulin antagonist in the manufacture or preparation of a medicament. In one embodiment, the neuregulin antagonist, or medicament manufactured with the neuregulin antagonist, is used to increase the time to tumor recurrence in a patient. In another embodiment, the neuregulin antagonist, or medicament manufactured with the neuregulin antagonist, is used to treat a patient with a cancer that is resistant to a therapeutic agent.

A. NRG Antagonists

NRG antagonists useful in the methods of the invention include polypeptides that specifically bind to NRG, NRG antibodies (anti-NRG antibodies), RNA, such as RNAi, siRNA, shRNA, etc., small molecules, receptor molecules and derivatives, such as immunoadhesins, which bind specifically to NRG. (see, for example, U.S. Pat. Nos. 6,696,290 and 7,659,368, US publications 2010055093 and 20100278801) and fusions proteins. NRG antagonists also include antagonistic variants of NRG polypeptides, RNA aptamers and peptibodies against NRG. Examples of each of these are described below. In one embodiment, the NRG antagonists are NRG1 antagonists. In other embodiments, the NRG antagonists are NRG2, NRG3, or NRG4 antagonists.

1. Antibodies

Anti-NRG antibodies that are useful in the methods of the invention include any antibody that binds with sufficient affinity and specificity to NRG and can reduce or inhibit NRG signaling. NRG antibodies are described in WO1992020798, U.S. Pat. No. 6,953,842, and U.S. Pat. No. 6,252,051.

a) Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

b) Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, M A; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

c) Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

d) Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*. 103:3557-3560 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

e) Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

f) Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for NRG and the other is for any other antigen. In certain embodiments, bispecific antibodies may bind to two different epitopes of NRG. Bispecific antibodies may also be used to localize cytotoxic agents to cells which express NRG. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/

089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to NRG as well as another, different antigen (see, US 2008/0069820, for example).

g) Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

h) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |

TABLE 1-continued

| Original Residue | Exemplary Substitutions | Preferred Substitutions |
|---|---|---|
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

i) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd).

Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

j) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

k) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

l) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

m) Recombinant Methods and Compositions

Antibodies may be produced using recombinant methods and compositions, e.g., as described in U.S. Pat. No. 4,816,567. In one embodiment, isolated nucleic acid encoding an anti-NRG antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-NRG antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-NRG antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

n) Assays

NRG antagonists provided herein may be identified, screened for, or characterized for their physical/chemical properties and/or biological activities by various assays known in the art.

In one aspect, an antibody of the invention is tested for its antigen binding activity, e.g., by known methods such as ELISA, Western blot, etc.

In another aspect, assays are provided for identifying NRG antagonists thereof having biological activity. Biological activity may include, e.g., inhibition of NRG induced receptor tyrosine kinase signaling, inhibition of tumor growth, inhibition of cellular proliferation. etc. Antagonists having such biological activity in vivo and/or in vitro are also provided.

In certain embodiments, an antagonist of the invention is tested for such biological activity. In one embodiment, the ability of an antagonist to inhibit NRG induced receptor tyrosine kinase signaling can be measured by determining the level of NRG induced phosphorylation of the tyrosine residues of receptor tyrosine kinases in the presence and absence of a potential NRG antagonist. Holmes, et al. 1992. The following is an exemplary assay to determine the phosphorylation state of receptor tyrosine kinases. Cells expressing Her2 and Her3 (such as Caov3 cells, or cells engineered to express Her2 and Her3) are stimulated with 10 nM NRG following a 60 minute pre-incubation with either the potential NRG antagonist or buffer (control). Whole cell lysates are analyzed on a Western blot probed with an anti-phosphotyrosine antibody to determine level of tyrosine phosphorylation. The blots may be scanned to quantitate the anti-phosphotyrosine signal. NRG antagonists would reduce the level of tyrosine phosphorylation as compared to the buffer control. In one embodiment, the NRG antagonist inhibits NRG induced tyrosine kinase signaling by at least 30%, 40%, 50%, 60% 70%, 80%, 85%, 90%, 95%, 96%, 97%, 98%, or 99% as compared to an untreated control.

In certain embodiments, an antibody of the invention is tested for its ability to inhibit cell growth or proliferation in vitro. Assays for inhibition of cell growth or proliferation are well known in the art. Certain assays for cell proliferation, exemplified by the "cell killing" assays described herein, measure cell viability. One such assay is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) *J. Immunol. Meth.* 160:81-88, U.S. Pat. No. 6,602,677. The assay may be conducted in 96- or 384-well format, making it amenable to automated high-throughput screening (HTS). See Cree et al (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

Another assay for cell proliferation is the "MTT" assay, a colorimetric assay that measures the oxidation of 3-(4,5-dimethylthiazol-2-yl)-2,5-diphenyltetrazolium bromide to formazan by mitochondrial reductase. Like the CellTiter-Glo™ assay, this assay indicates the number of metabolically active cells present in a cell culture. See, e.g., Mosmann (1983) *J. Immunol. Meth.* 65:55-63, and Zhang et al. (2005) *Cancer Res.* 65:3877-3882.

In one aspect, a NRG antagonist is tested for its ability to induce cell death in vitro. Assays for induction of cell death are well known in the art. In some embodiments, such assays measure, e.g., loss of membrane integrity as indicated by uptake of propidium iodide (PI), trypan blue (see Moore et al. (1995) *Cytotechnology,* 17:1-11), or 7AAD. In an exemplary PI uptake assay, cells are cultured in Dulbecco's Modified Eagle Medium (D-MEM):Ham's F-12 (50:50) supplemented with 10% heat-inactivated FBS (Hyclone) and 2 mM L-glutamine Thus, the assay is performed in the absence of complement and immune effector cells. Cells are seeded at a density of $3\times10^6$ per dish in 100×20 mm dishes and allowed to attach overnight. The medium is removed and replaced with fresh medium alone or medium containing various concentrations of the antibody or immunoconjugate. The cells are incubated for a 3-day time period. Following treatment, monolayers are washed with PBS and detached by trypsinization. Cells are then centrifuged at 1200 rpm for 5 minutes at 4° C., the pellet resuspended in 3 ml cold $Ca^{2+}$ binding buffer (10 mM Hepes, pH 7.4, 140 mM NaCl, 2.5 mM $CaCl_2$) and aliquoted into 35 mm strainer-capped 12×75 mm tubes (1 ml per tube, 3 tubes per treatment group) for removal of cell clumps. Tubes then receive PI (10 µg/ml). Samples are analyzed using a FACSCAN™ flow cytometer and FACSCONVERT™ CellQuest software (Becton Dickinson). Antibodies which induce statistically significant levels of cell death as determined by PI uptake are thus identified.

In one aspect, a NRG antagonist is tested for its ability to induce apoptosis (programmed cell death) in vitro. An exemplary assay for antibodies or immunoconjugates that induce apoptosis is an annexin binding assay. In an exemplary annexin binding assay, cells are cultured and seeded in dishes as discussed in the preceding paragraph. The medium is removed and replaced with fresh medium alone or medium containing 0.001 to 10 µg/ml of the antibody or immunoconjugate. Following a three-day incubation period, monolayers are washed with PBS and detached by trypsinization. Cells are then centrifuged, resuspended in $Ca^{2+}$ binding buffer, and aliquoted into tubes as discussed in the preceding paragraph. Tubes then receive labeled annexin (e.g. annexin V-FITC) (1 µg/ml). Samples are analyzed using a FACSCAN™ flow cytometer and FACSCONVERT™ CellQuest software (BD Biosciences). Antibodies that induce statistically significant levels of annexin binding relative to control are thus identified. Another exemplary assay for antibodies or immunoconjugates that induce apoptosis is a histone DNA ELISA colorimetric assay for detecting internucleosomal degradation of genomic DNA. Such an assay can be performed using, e.g., the Cell Death Detection ELISA kit (Roche, Palo Alto, Calif.).

Cells for use in any of the above in vitro assays include cells or cell lines that naturally express NRG or that have been engineered to express NRG. Such cells include tumor cells that overexpress NRG relative to normal cells of the same tissue origin. Such cells also include cell lines (including tumor cell lines) that express NRG and cell lines that do not normally express NRG but have been transfected with nucleic acid encoding NRG.

In one aspect, a NRG antagonist is tested for its ability to inhibit cell growth or proliferation in vivo. In certain embodiments, a NRG antagonist is tested for its ability to inhibit tumor growth in vivo. In vivo model systems, such as xenograft models, can be used for such testing. In an exemplary xenograft system, human tumor cells are introduced into a suitably immunocompromised non-human animal, e.g., an athymic "nude" mouse. An antibody of the invention is administered to the animal. The ability of the antibody to inhibit or decrease tumor growth is measured. In certain embodiments of the above xenograft system, the human tumor cells are tumor cells from a human patient. Such xenograft models are commercially available from Oncotest GmbH (Frieberg, Germany). In certain embodiments, the human tumor cells are cells from a human tumor cell line. In certain embodiments, the human tumor cells are introduced into a suitably immunocompromised non-human animal by subcutaneous injection or by transplantation into a suitable site, such as a mammary fat pad.

In certain embodiments, the NRG antagonist inhibits cellular proliferation by at least 30%, 40%, 50%, 60% 70%, 80%, 85%, 90%, 95%, 96%, 97%, 98%, or 99% as compared to an untreated control. In other embodiments, the NRG antagonist inhibits tumor growth by at least 30%, 40%, 50%, 60% 70%, 80%, 85%, 90%, 95%, 96%, 97%, 98%, or 99% as compared to an untreated control.

2. NRG Binding Polypeptides

NRG binding polypeptides or fragments thereof that specifically bind to NGR can be used in the methods of the invention, e.g., to bind to and sequester the NGR protein, thereby preventing it from signaling. Preferably, the NRG polypeptides or fragment thereof, is a soluble form. In some embodiments, a soluble form of the polypeptide exerts an inhibitory effect on the biological activity of the NGR by binding to NGR, thereby preventing it from associating with its natural binding partners.

3. Aptamers

Aptamers are nucleic acid molecules that form tertiary structures that specifically bind to a target molecule, such as a NRG polypeptide. The generation and therapeutic use of aptamers are well established in the art. See, e.g., U.S. Pat. No. 5,475,096. Additional information on aptamers can be found in U.S. Patent Application Publication No. 20060148748.

4. Peptibody

A peptibody is a peptide sequence linked to an amino acid sequence encoding a fragment or portion of an immunoglobulin molecule. Polypeptides may be derived from randomized sequences selected by any method for specific binding, including but not limited to, phage display technology. In a preferred embodiment, the selected polypeptide may be linked to an amino acid sequence encoding the Fc portion of an immunoglobulin. Peptibodies that specifically bind to and antagonize NRG are also useful in the methods of the invention.

5. Antagonistic Nucleic Acids

Other NRG antagonists are antisense RNA or DNA constructs prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature NRG polypeptide herein, can be used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science,* 251:1360 (1991)), thereby preventing transcription and the production of the NRG polypeptide. The antisense RNA oligonucleotide hybridizes to the mRNA in vivo and blocks translation of the mRNA molecule into the NRG polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the NRG polypeptide. When antisense DNA is used, oligodeoxyribonucleotides derived from the translation-initiation site, e.g., between about −10 and +10 positions of the target gene nucleotide sequence, are preferred.

Small interfering RNAs (siRNAs) are double stranded RNA molecules generally less than 30 nucleotides in length that reduce expression of a target gene. siRNAs have proven useful as a tool in studies of modulating gene expression where traditional antagonists such as small molecules or antibodies have failed. (Shi Y., Trends in Genetics 19(1):9-12 (2003)). In vitro synthesized, double stranded RNAs that are 21 to 23 nucleotides in length can act as interfering RNAs (iRNAs) and can specifically inhibit gene expression (Fire A., Trends in Genetics 391; 806-810 (1999)). These iRNAs act by mediating degradation of their target RNAs. Since they are under 30 nucleotides in length, however they do not trigger a cell antiviral defense mechanism. In some embodiments of the invention, the siRNA has at least about 90%, 91%, 92%, 93%, 94%, 95%, 96%, 97%, 98%, 99%, or 100% nucleic acid sequence identity with a portion of the coding sequence of the NRG encoding polynucleotide or its complement.

6. Oligopeptides

NRG binding oligopeptides of the invention are oligopeptides that bind, preferably specifically, to NRG as described herein. NRG binding oligopeptides may be chemically synthesized using known oligopeptide synthesis methodologies or may be prepared and purified using recombinant technology. NRG binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a NRG as described herein. NRG binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) *Science*, 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA*, 87:6378) or protein (Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

7. Small Molecules

NRG binding small molecules are, in some embodiments, organic molecules other than oligopeptides or antibodies as defined herein that bind, preferably specifically, to NRG as described herein. NRG binding organic small molecules may be identified and chemically synthesized using known methodology (see, e.g., PCT Publication Nos. WO00/00823 and WO00/39585). NRG binding organic small molecules are usually less than about 2000 daltons in size, alternatively less than about 1500, 750, 500, 250 or 200 daltons in size, wherein such organic small molecules that are capable of binding, preferably specifically, to NRG as described herein may be identified without undue experimentation using well known techniques. In this regard, it is noted that techniques for screening organic small molecule libraries for molecules that are capable of binding to a polypeptide target are well known in the art (see, e.g., PCT Publication Nos. WO00/00823 and WO00/39585). NRG binding organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

8. Immunoconjugates

The invention also provides immunoconjugates comprising an NRG antagonist herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

B. Methods and Compositions for Diagnostics and Detection

In certain embodiments, NRG antagonists provided herein are useful for detecting the presence of NRG in a biological sample. The term "detecting" as used herein encompasses quantitative or qualitative detection. In certain embodiments, a biological sample comprises a cell or tissue, such as lung tissue or breast tissue.

In one embodiment, an anti-NRG antibody for use in a method of diagnosis or detection is provided. In a further aspect, a method of detecting the presence of NRG in a biological sample is provided. In certain embodiments, the method comprises contacting the biological sample with an anti-NRG antibody as described herein under conditions permissive for binding of the anti-NRG antibody to NRG, and detecting whether a complex is formed between the anti-NRG antibody and NRG. Such method may be an in vitro or in vivo method. In one embodiment, an anti-NRG antibody is used to select subjects eligible for therapy with an anti NRG antibody, e.g. where NRG is a biomarker for selection of patients.

In one embodiment, a patient is selected for treatment with an NRG antagonist if the patient has a cancer which is or is likely to become resistant to therapy. One aspect of the invention provides for an assay which determines if a patient has a cancer which is or is likely to become resistant to therapy. In one embodiment, the assay comprises assaying tumor cells taken from the patient for NRG expression, wherein expression of NRG is indicative that the patient has a cancer which is or is likely to become resistant to therapy. In one embodiment, the patient is selected as one who has a cancer which or is likely to become resistant to therapy if the level of NRG expression in the tumor is less than the level of NRG expression in the TRICs of the tumor.

In one embodiment, a patient is selected for treatment with an NRG antagonist if the patient has a cancer which is likely to relapse after treatment with a therapeutic agent. One aspect of the invention provides for an assay which determines if a patient has a cancer which is likely to relapse after treatment with a therapeutic agent. In one embodiment, the assay comprises assaying tumor cells taken from the patient for NRG expression, wherein expression of NRG is indicative that the patient has a cancer which is likely to relapse after treatment with a therapeutic agent. In one embodiment, the patient is selected as one who has a cancer which is likely to relapse after treatment with a therapeutic agent if the level of NRG expression in the tumor is less than the level of NRG expression in the TRICs of the tumor.

In certain embodiments, a diagnostic assay comprises determining the expression of neuregulin in a tumor cell, using, for example, immunohistochemistry, in situ hybridization, or RT-PCR. In other embodiments, a diagnostic assay comprises determining expression levels of neuregulin in a tumor cell using, for example, quantitative RT-PCR. In some embodiments, a diagnostic assay further comprises determining expression levels of neuregulin compared to a control tissue such as, for example, non-cancerous adjacent tissue.

In certain embodiments, labeled anti-NRG antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

C. Therapeutic Methods and Compositions

The NRG antagonists provided herein may be used in therapeutic methods.

In one aspect, a NRG antagonist for use as a medicament is provided. In further aspects, a NRG antagonist for use in treating cancer is provided. In certain embodiments, a NRG antagonist for use in a method of treatment is provided. In certain embodiments, the invention provides a NRG antagonist for use in a method of treating an individual having cancer comprising administering to the individual an effective amount of a NRG antagonist. In one such embodiment, the method further comprises administering to the individual an effective amount of at least one additional therapeutic agent, e.g., as described below. In further embodiments, the invention provides a NRG antagonist for use in treating a patient who has experienced a recurrence of cancer. In certain embodiments, the invention provides a NRG antagonist for use in a method of preventing resistance to treatment with a therapeutic agent in an individual comprising administering to the individual an effective of the a NRG antagonist to prevent resistance to the therapeutic agent.

In a further aspect, the invention provides for the use of a NRG antagonist in the manufacture or preparation of a medicament. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. In a further embodiment, the medicament is for preventing resistance to treatment with a therapeutic agent in patient. In a further embodiment, the medicament is for preventing recurrence of cancer in a patient.

In a further aspect, the invention provides pharmaceutical formulations comprising any of the NRG antagonists provided herein, e.g., for use in any of the above therapeutic methods. In one embodiment, a pharmaceutical formulation comprises any of the NRG antagonists provided herein and a pharmaceutically acceptable carrier. In another embodiment, a pharmaceutical formulation comprises any of the NRG antagonists provided herein and at least one additional therapeutic agent, e.g., as described below.

One embodiment provides pharmaceutical compositions or medicaments containing a NRG antagonist and a therapeutically inert carrier, diluent or excipient, as well as methods of using the compounds of the invention to prepare such compositions and medicaments. In one example, compounds may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound is formulated in an acetate buffer, at pH 5. In another embodiment, the compounds are sterile. The compound may be stored, for example, as a solid or amorphous composition, as a lyophilized formulation or as an aqueous solution.

Pharmaceutical formulations of a NRG antagonist as described herein are prepared by mixing such antagonist having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO2006/044908, the latter formulations including a histidine-acetate buffer.

Compositions are formulated, dosed, and administered in a fashion consistent with good medical practice. Factors for consideration in this context include the particular disorder being treated, the particular patient being treated, the clinical condition of the individual patient, the cause of the disorder, the site of delivery of the agent, the method of administration, the scheduling of administration, and other factors known to medical practitioners.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

In one example, the pharmaceutically effective amount of the NRG antagonist administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, preferably contain from about 5-100 mg of the compound of the invention.

The NRG antagonists may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

The NRG antagonist may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound, or a stereoisomer or pharmaceutically acceptable salt thereof. In a further embodiment includes a pharmaceutical composition comprising a compound, or a stereoisomer or pharmaceutically acceptable salt thereof, together with a pharmaceutically acceptable carrier or excipient.

In the case of an antibody, the antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to a NRG antagonist.

NRG antagonists of the invention can be used either alone or in combination with other agents in a therapy. For instance, a NRG antagonist of the invention may be co-administered with at least one additional therapeutic agent.

In certain embodiments, an additional therapeutic agent is an agent that inhibits a tyrosine kinase receptor pathway. In one embodiment, the additional therapeutic agent inhibits a HER pathway. In one embodiment the additional therapeutic agent is an inhibitor of EGFR, HER2, HER3, and/or HER4.

As used herein, the term "EGFR inhibitor" refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29):30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654, 307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl) amino]-7-[3-(4-morpholinyl)propoxy]-6-quinazolinyl]-, dihydrochloride, Pfizer Inc.); ZD1839, gefitinib (IRESSA™) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N-8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl) amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl] 6[5[[[2methylsulfonyl) ethyl]amino]methyl]-2-furanyl]-4-quinazolinamine; GlaxoSmithKline).

As used herein, the term "HER2 inhibitor" refers to compounds that bind to or otherwise interact directly with HER2 and prevent or reduce its signaling activity, and is alternatively referred to as an "HER2 antagonist." Examples of such agents include antibodies and small molecules that bind to HER2. Particular HER2 antibodies include pertuzumab and trastuzumab. As used herein, the term "HER3 inhibitor" refers to compounds that bind to or otherwise interact directly with HER3 and prevent or reduce its signaling activity, and is alternatively referred to as an "HER3 antagonist." Examples of such agents include antibodies and small molecules that bind to HER3. As used herein, the term "HER4 inhibitor" refers to compounds that bind to or otherwise interact directly with HER4 and prevent or reduce its signaling activity, and is alternatively referred to as an "HER4 antagonist." Examples of such agents include antibodies and small molecules that bind to HER4.

Patent publications related to HER antibodies include: U.S. Pat. Nos. 5,677,171, 5,720,937, 5,720,954, 5,725,856, 5,770,195, 5,772,997, 6,165,464, 6,387,371, 6,399,063, US2002/0192211A1, U.S. Pat. Nos. 6,015,567, 6,333,169, 4,968,603, 5,821,337, 6,054,297, 6,407,213, 6,719,971, 6,800,738, US2004/0236078A1, U.S. Pat. Nos. 5,648,237, 6,267,958, 6,685,940, 6,821,515, WO98/17797, U.S. Pat. Nos. 6,333,398, 6,797,814, 6,339,142, 6,417,335, 6,489, 447, WO99/31140, US2003/0147884A1, US2003/0170234A1, US2005/0002928A1, U.S. Pat. No. 6,573,043, US2003/0152987A1, WO99/48527, US2002/0141993A1, WO01/00245, US2003/0086924, US2004/0013667A1, WO00/69460, WO01/00238, WO01/15730, U.S. Pat. No. 6,627,19681, U.S. Pat. No. 6,632,979B1, WO01/00244, US2002/0090662A1, WO01/89566, US2002/0064785, US2003/0134344, WO 04/24866, US2004/0082047, US2003/0175845A1, WO03/087131, US2003/0228663, WO2004/008099A2, US2004/0106161, WO2004/048525, US2004/0258685A1, U.S. Pat. Nos. 5,985,553, 5,747,261, 4,935,341, 5,401,638, 5,604,107, WO 87/07646, WO 89/10412, WO 91/05264, EP 412,116 B1, EP 494,135 B1, U.S. Pat. No. 5,824,311, EP 444,181 B1, EP 1,006,194 A2, US 2002/0155527A1, WO 91/02062, U.S. Pat. Nos. 5,571, 894, 5,939,531, EP 502,812 B1, WO 93/03741, EP 554,441 B1, EP 656,367 A1, U.S. Pat. Nos. 5,288,477, 5,514,554, 5,587,458, WO 93/12220, WO 93/16185, U.S. Pat. No. 5,877,305, WO 93/21319, WO 93/21232, U.S. Pat. No. 5,856,089, WO 94/22478, U.S. Pat. Nos. 5,910,486, 6,028, 059, WO 96/07321, U.S. Pat. Nos. 5,804,396, 5,846,749, EP 711,565, WO 96/16673, U.S. Pat. Nos. 5,783,404, 5,977, 322, 6,512,097, WO 97/00271, U.S. Pat. Nos. 6,270,765, 6,395,272, 5,837,243, WO 96/40789, U.S. Pat. Nos. 5,783, 186, 6,458,356, WO 97/20858, WO 97/38731, U.S. Pat. Nos. 6,214,388, 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53354, WO 01/56604, WO 01/76630, WO02/05791, WO 02/11677, U.S. Pat. No. 6,582,919, US2002/0192652A1, US 2003/0211530A1, WO 02/44413, US 2002/0142328, U.S. Pat. No. 6,602,670 B2, WO 02/45653, WO 02/055106, US 2003/0152572, US 2003/0165840, WO 02/087619, WO 03/006509, WO03/012072, WO 03/028638, US 2003/0068318, WO 03/041736, EP 1,357,132, US 2003/0202973, US 2004/0138160, U.S. Pat. Nos. 5,705,157, 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842, WO 03/86467, and US 2010/0255010.

In certain embodiments, an additional therapeutic agent is a chemotherapeutic agent. A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1 (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), pegylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTACC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

Such combination therapy also includes: (i) lipid kinase inhibitors; (ii) antisense oligonucleotides, particularly those which inhibit expression of genes in signaling pathways implicated in abherant cell proliferation, such as, for example, PKC-alpha, Ralf and H-Ras; (iii) ribozymes such as a VEGF expression inhibitor (e.g., ANGIOZYME® ribozyme) and a HER2 expression inhibitor; (iv) vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; (v) anti-angiogenic agents such as bevacizumab (AVASTIN®, Genentech); and pharmaceutically acceptable salts, acids or derivatives of any of the above.

Such combination therapies noted above encompass combined administration (where two or more therapeutic agents are included in the same or separate formulations), and separate administration, in which case, administration of the NRG antagonist of the invention can occur prior to, simultaneously, and/or following, administration of the additional therapeutic agent and/or adjuvant. NRG antagonists of the invention can also be used in combination with radiation therapy.

D. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

Example 1

Methods

Cell Lines

NSCLC cell lines Calu3, H441, H1299, H1993, A549 and H596, and KPL4 breast cancer cell line were obtained from American Type Culture Collection (ATCC), Manassas, Va. These cell lines were maintained in RPMI containing 10% FBS, Pen/Strep and L-Glutamine. Calu3 was cultured in ATCC media instead of RPMI. Calu3, H441 and KPL4 cell lines were transduced with TZV-b-actin-eGFP lentivirus. After multiple passages, high GFP expressing cells were sorted and amplified to get ~95% GFP positive cells, and these sub-lines were described as Calu3-GFP and H441-GFP and KPL4-GFP. Mouse NSCLC cell lines LKPH1 and LKPH2 were derived from two independent tumors from a $Kras^{LSL-G12D/+}$; $p53^{FL/+}$; Z/EG lung tumor-bearing mouse. Cell lines were initially established in DMEM/F12 media containing 5% FBS, Bovine Pituitary Extract, N2 supplement, EGF, FGF, Pen/Strep and L-Glutamine LKPH1 and LKPH2 were cultured in DMEM high-glucose media containing 10% FBS, Pen/Strep and L-Glutamine.

Inducible shRNA lentivirus: Hairpin oligonucleotides used in this study are as follows:

```
shNRG1:
                                           (SEQ ID NO: 1)
5'- GATCCCCCATGGTGAACATAGCGAATTTCAAGAGAATTCGCTAT

GTTCACCATGTTTTTTGGAAA-3' (sense)
and (SEQ ID NO: 2)
5'- AGCTTTTCC AAAAAACATGGTGAACAT AGC GAATTCTCTTG AAATTCGCTATGTTCACCATGGGG-3' (antisense).

shNRG1.2:
                                           (SEQ ID NO: 3)
5'GATCCCCGAGTATATGTGCAAAGTGAT TCAAGAGATCAC TTTGC

ACATATACTCTTTTTGGAAA-3' (sense)
and (SEQ ID NO: 4)
5'-AGCTTTTCCAAAAAGAGTATATGTGCAAAGTGATCTCTTGAATC ACTTTGCACATATACTCGGG-3' (antisense).

shErbB4:
                                           (SEQ ID NO: 5)
5'-GATCCCCGATCACAACTGCTGCTTAATTCAAGAGATTAAGCAGCA

GTTGTGATCTTTTTTGGAAA-3" (sense)
``` and

```
                                            (SEQ ID NO: 6)
5' AGCTTTTCCAAAAAAGATCACAACTGCTGCTTAATCTCTTGA AT

TAAGCAGCAGTTGTGATCGGG-3' (antisense).

shErbB3:
                                            (SEQ ID NO: 7)
5'-GATCCCCAAGAGGATGTCAACGGTTATTCAAGAGATAACCGTTGA

CATCCTCTTTTTTTTGGAAA-3' (sense)
and
                                            (SEQ ID NO: 8)
5'-AGCTTTTCCAAAAAAAGAGGATGTCAACGGTTATCTCTTGAATA ACCGTTGACATCCTCTTGGG-3' (antisense).

Mouse shNRG1:
                                            (SEQ ID NO: 9)
5"-GATCCCCCATGGTGAACATAGCGAATTTCA AGAGAATTCGCTAT GTTCACCATGTTTTTGGAAA-3' (sense)
and
                                            (SEQ ID NO: 10)
5'-AGCTTTTCC AAAAAACATGGTGAACATAGC GAATTCTCTTGAA ATTCG CTATGTTCACCATGGGG-3" (antisense).
```

The complementary double-stranded shRNA oligonucleotides were inserted into a Tet-inducible viral gene transfer vector as described (Hoeflich et al. Cancer Res. 2006). The vector system is composed of a shuttle vector and a dsRed expressing viral vector backbone that contains a codon-optimized Tet repressor-internal ribosomal entry site-dsRed cassette to enable Tet-regulated shRNA expression. The luciferase shRNA construct was previously described (Hoeflich et al.).

Viral packaging and cell line generation: Inducible-shRNA bearing lentivirus constructs were made based on previously described methods by co-transfectiner pHUSH-Lenti-dsRed constructs containing a desired shRNA with plasmids expressing the vesicular stomatitis virus (VSV-G) envelope glycoprotein and HIV-1 packaging proteins (GAG-POL) in HEK293T cells using Lipofectamine (invitrogen, Carlsbad, Calif.). Target cells were transduced with these viruses. After >3 passages, FACS sorting was used to select the top ~20% dsRed expressing tumor cells which were collected, pooled and expanded.

In vitro studies: To induce shRNA expression, stable cell lines harboring doxycycline-inducible shNRG1 or shLuciferase were grown in 1 ug/ml doxycycline for a total of 6 days. The first day of induction cells were grown in 10% FBS, followed by a titration of FBS over the course of 4 more days. The cells were then completely serum starved during the last 6 hours of growth. Cells were then processed for RNA extraction or western blotting. For HER4ECD studies in mouse lung tumor cell lines, LKPH cells were grown in serum starved conditions for 24 hours prior to addition of HER4ECD at a concentration of 2 mg/ml. LKPH cells were then incubated for another 48 hours prior to processing for Western blotting. Addition of exogenous NRG1 on H441 cells were performed as follows: H441 cells were serum starved for 18 hours prior to addition of 1 uM recombinant human NRG1 beta-1 extracellular domain (R&D systems) or 1 uM anti-ragweed IgG2A as the control. Ten minutes after addition of NRG1 or ragweed, cells were processed for Western blotting.

RNA Isolation, cDNA preparation and qPCR: RNA was isolated using the Qiagen RNeasy Micro Kit. Complementary DNA was prepared from total RNA using ABI high fidelity kit according to manufacturer's instructions. NRG1alpha, NRG1beta, HER3, HER4 expression was determined using ABI gene specific primers/probe by quantitative real time PCR (ABI 7500). Gene expression was normalized using GAPDH or RAB 14 house keeping genes.

In vivo xenograft tumor studies: Tumor cells (10-20 million) were transplanted into right flank of athymic nude mice. When tumor size reached ~200 mm$^3$, the mice were divided into different treatment groups. Mice were then treated with either vehicle or chemotherapy (paclitaxel, i.v.+cisplatin, i.p.) for the initial studies. The chemotherapy dosing regimen was paclitaxel 20 mg/kg i.v. every other day for 5 doses and cisplatin 5 mg/kg i.p. on days 1 and 7 for the Calu3 model and days 1 and 14 for the H441 model. Regressed tumors and time matched vehicle controls were collected at least 1 week after the last dose of chemo. Tumors were dissociated using dispase/collagenase and samples were FACS sorted to collect the GFP positive tumor cells. For the NRG1 knockdown studies, the treatment groups were: sucrose, doxycycline (dox), chemotherapy+sucrose, and chemotherapy+doxycycline. Treatment with sucrose or doxycycline was started at the same time as the first dose of chemotherapy and continued for the duration of the study. 5% sucrose water was provided ad libitum for the vehicle groups and 1 mg/ml doxycycline in 5% sucrose was provided for the doxycycline groups.

Xenograft Tumor Growth Analysis: To appropriately analyze the repeated measurement of tumor volumes from the same animals over time, a mixed-modeling approach was used (Pinheiro et al. 2009). This approach can address both repeated measurements and modest drop-out rate due to nontreatment-related termination of animals prior to study end. Cubic regression splines were used to fit a nonlinear profile to the time courses of log 2 tumor volume for each treatment group.

In vivo LSL-K-ras$^{G12D}$; p53$^{Fl/+}$ and LSL-K-ras$^{G12D}$; p53$^{Fl/Fl}$ Her4ECD study: LSL-K-ras$^{G12D}$; p53$^{Fl/+}$ were infected with Adeno-Cre virus and allowed to age for 16 weeks post-tumor induction. Baseline CT scans were performed at 16 weeks post-tumor induction (day 0 of study) and mice were grouped such that average starting tumor volume per group were equal. Mice were dosed once a week for three weeks with cisplatin (7 mg/kg) or phosphate-buffered saline, and bi-weekly with HER4ECD-Fc (25 mg/kg) or anti-ragweed IgG2A (25 mg/kg) for the duration of the study. Serial CT scans were performed at days 14, 45, and 66.

X-ray micro-computed tomography (micro-CT): Two micro-CT systems (vivaCT 40 and vivaCT 75, Scanco Medical, Switzerland) were utilized for longitudinal lung imaging. Animals were randomized between micro-CT systems and rescanned on the same system used for baseline imaging. Data was acquired at 38 μm (vivaCT 40) or 50 μm (vivaCT 75) isotropic voxel size, 1000 projections, 250 ms (vivaCT 40) or 200 ms (vivaCT 75) integration time, 45 keV photon energy, and 177 mA current. For the duration of the in-vivo imaging, the animals were anesthetized with 2% isoflurane in medical air and maintained at constant 37° C. temperature by regulated warm airflow. The imaging time for each session was approximately 15 minutes (vivaCT 75) or 25 minutes (vivaCT 40) per animal and the estimated radiation dose was approximately 0.2 Gy (vivaCT 75) or 0.1 Gy (vivaCT 40). The imaging data were evaluated in the coronal plane using the image analysis software package Analyze (AnalyzeDirect, Inc., Lenexa, Kans., USA). Once the largest cross-sectional plane of each tumor was identified, estimates of maximal tumor diameter ($d_1$) and the largest perpendicular diameter ($d_2$) were determined The total tumor burden was calculated as the sum of the cross-product of the directional estimates ($d_1 \times d_2$) of all the tumors. In-vivo micro-CT tumor analysis was previously validated and was found to be well correlated with the total tumor volume as determined by ex-vivo microCT analysis (Singh et al., 2010).

Microarray Analysis: The quantity of total RNA used in two round T7 amplification protocol ranged from 10 ng to 50 ng per sample. First round of amplification and second round cDNA synthesis were done using Message Amp II aRNA Amplification kit (Applied Biosystems, Foster City, Calif.). Cye-5 dye was then incorporated through an IVT reaction using Agilent's Quick Amp Labeling kit (Agilent Technologies, Palo Alto, Calif.). Each Cy-5 labeled test sample was pooled with Cy-3 labeled Universal Human Reference RNA (Agilent Technologies, Palo Alto, Calif.) and hybridized onto Agilent's Whole Human Genome 4×44K arrays as described in manufacturer's protocol. The arrays were washed, dried and scanned on Agilent's DNA microarray scanner. Agilent's Feature Extraction software 9.5 was used to analyze acquired array images and Individual log 2 ratios of background subtracted signal intensities were obtained. A modified Cybert-T test (Baldi and Long, 2001) was performed to compare the expression profiles between the vehicle treated and chemotherapy groups. A false discovery rate (qvalue) was applied for multiple testing corrections (Storey and Tibshirani, 2003)

siRNA: Small interfering RNA oligo (siRNA) pools for HER3 (M-003127-03), HER1 (M-003114-01). HER2, HER4 and non targeting control (D-001206-14-20) were purchased from Dharmacon Lafayette, Colo. siRNAs were introduced into H522 cells by reverse transfection. cells/well were seeded in 96 well microtiter plates containing a pre-incubated mix of pooled RNAi oligos at 50 mmol/L and DharmaFECT# (T-2001-02, Dharmacon) transfection reagent diluted in OPTI-MEM (Invitrogen) as per manufacturer's recommendation. 96 h post transfection the effect on cell proliferation was measured by AlamarBlue staining.

Western Blotting: For Western blots of in vitro cell culture, adherent cells were washed three times with ice cold 1× phosphate-buffered saline (PBS) and lysed in RIPA buffer (Pierce Biotechnology), Halt protease inhibitor, and Halt phosphatase inhibitor cocktail (Thermo Scientific). The lysate was collected, homogenized, and clarified by centrifuging for 10 minutes. Primary mouse tumor lysates were prepared as stated above, without the PBS washes. Supernatant proteins were fractionated in a 4-12% NuPAGE Novex bis-tris gel (Invitrogen). Blotting was carried out using the iBlot dry blotting system (Invitrogen) according to manufacturer's specifications. Nitrocellulose membrane blocking and antibody staining was performed using the Odyssey Western blot analysis and infrared imaging system (Li-Cor Biosciences) according to manufacturer's instructions. Blots were visualized on the Odyssey scanner (Li-Cor Biosciences).

Antibodies: The following primary antibodies were used in Western blotting experiments: anti-actin (612656, BD Biosciences), anti-GAPDH (sc-25778, Santa Cruz Biotechnology), anti-EGF receptor (2232, Cell Signaling Technology), anti-Neu (sc-284, Santa Cruz Biotechnology), anti-ErbB3 (sc-285, Santa Cruz Biotechnology), anti-phospho-HER3 (4791, Cell Signaling Technology), anti-ErbB4 (sc-283, Santa Cruz Biotechnology), anti-phospho-HER4 (4757, Cell Signaling Technology), anti-Akt (4691, Cell Signaling Technology), anti-phospho-Akt (4058, Cell Signaling Technology), Stat/phospho-Stat antibody sampler kit (9939/9914, Cell Signaling Technology), anti-MEK 1/2 (9126, Cell Signaling Technology), anti-phospho-MEK 1/2 (2338, Cell Signaling Technology). The following secondary antibodies from Li-Cor Biosciences were used: IRDye 680 conjugated goat anti-mouse IgG, IRDye 800 CW conjugated goat anti-rabbit IgG.

Example 2

Optimization of In Vivo Models for the Study of Residual Disease and Relapse

Several cancer models that show significant regression in response to chemotherapy followed by tumor relapse after the cessation of therapy (FIG. 1) were generated and used to study the cells that are responsible for tumor re-initiation. These cells are tumor reinitiating cells (TRICs). In order to generate the models, GFP labeled human tumor cells were transplanted subcutaneously, and when tumor size reached ~200 mm³, mice were treated with either vehicle or chemotherapy as shown in the respective models. GFP+ tumor cells were isolated from regressed or vehicle treated tumors by FACS-sorting after enzymatic digestion and dissociation. Tumors were collected a minimum of one week after the last dose of chemotherapy and before the resumption of tumor growth.

Figure 2A:
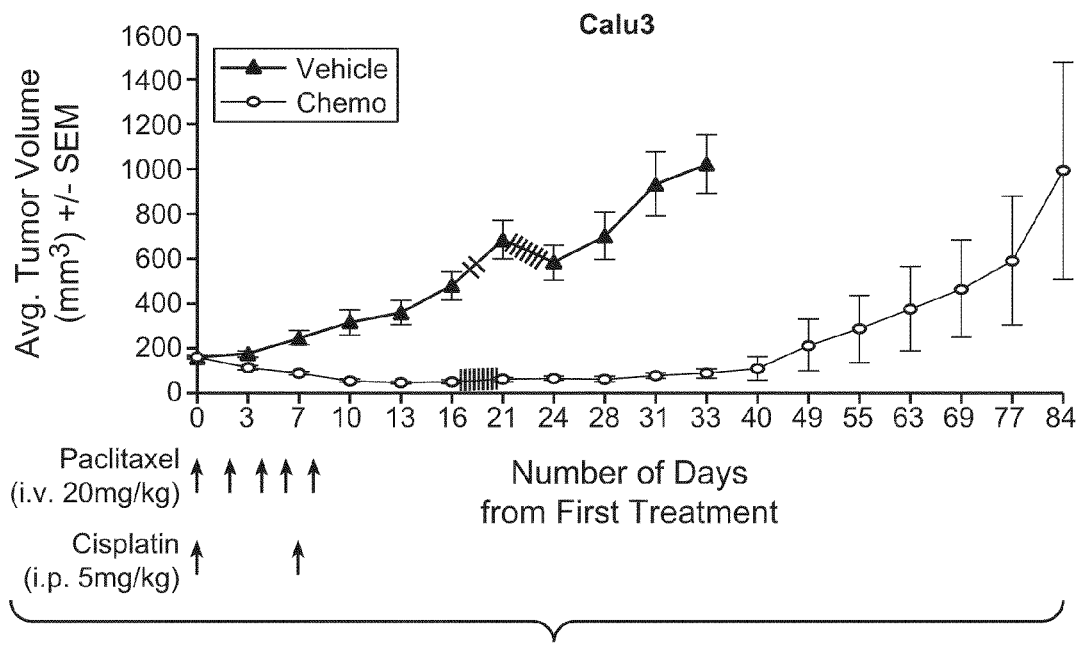
FIG. 2A. Calu3 human NSCLC xenograft model in athymic nude mice wherein chemotherapy consisted of paclitaxel and cisplatin. Data presented as mean tumor volume±SEM, n=12 mice/group.
Figure 2B:
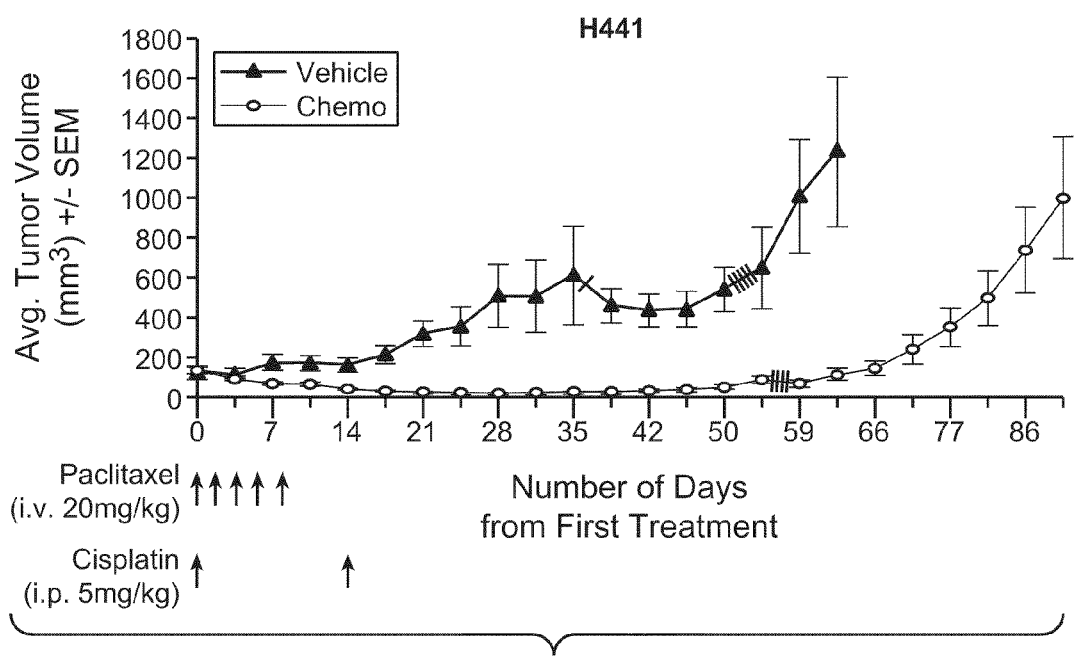
FIG. 2B. H441 human NSCLC xenograft model in athymic nude mice wherein chemotherapy consisted of paclitaxel and cisplatin. Data presented as mean tumor volume±SEM, n=12 mice/group.

GFP-expressing sublines of the human non-small cell lung cancer (NSCLC) cell lines Calu3 and H441 were transplanted into athymic nude mice to generate the xenograft models. For the Calu3 model, chemotherapy consisted of paclitaxel (20 mg/kg, i.v. every other day for 5 doses) and cisplatin (5 mg/kg, i.p. every 7 days for 2 doses). FIG. 2A (data presented as mean tumor volume±SEM, n=15/group). For the H441 model, chemotherapy consisted of paclitaxel (20 mg/kg, i.v. every other day for 5 doses) and cisplatin (5 mg/kg, i.p. every 14 days for 2 doses). FIG. 2B (data presented as mean tumor volume±SEM, n=9/group for vehicle treated and n=14/group for chemotherapy treated).

Figure 2C:
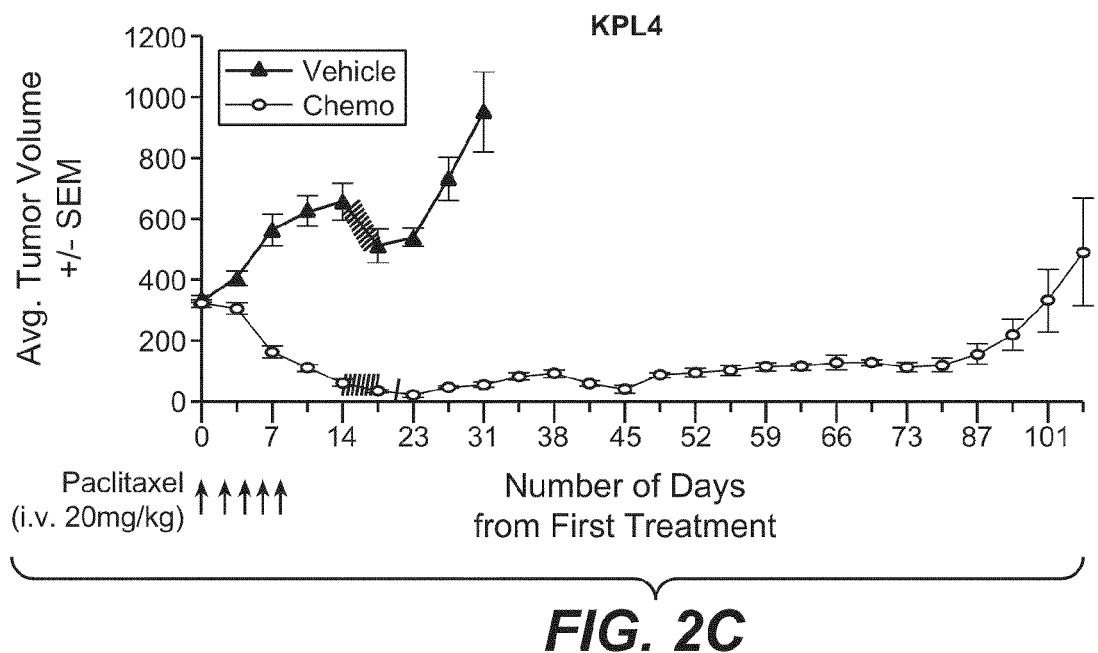
FIG. 2C. KPL4 human breast model with orthotropic transplantation of tumor cells to mammary fat pad of SCID/beiz mice wherein chemotherapy consisted of paclitaxel. Data presented as mean tumor volume±SEM, n=12 mice/group.

GFP-expressing sublines of the human breast cancer cell line KPL4 were transplanted orthotropically to the mammary fat pad of SCID/beiz mice. For the KPL4 model, chemotherapy consisted of Paclitaxel (20 mg/kg, i.v. every other day for 5 doses). FIG. 2C (data presented as mean tumor volume±SEM, n=12 mice/group).

Following completion of the chemotherapy regimen, the tumors of chemo-treated mice were significantly smaller than vehicle-treated mice. Regression persisted for several weeks after the last dose of chemotherapy but the tumors subsequently recurred. FIG. 2A-C.

Figure 2D:
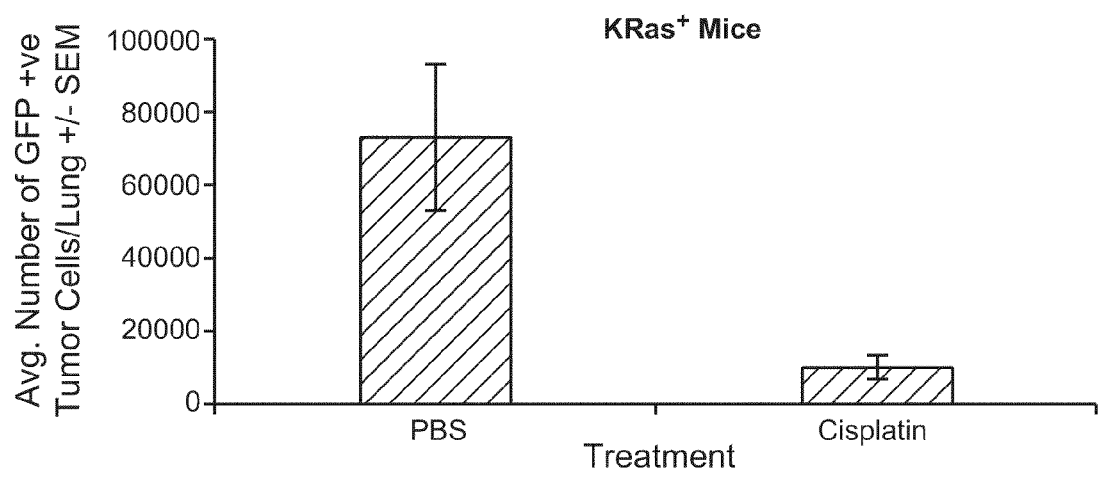
FIG. 2D. Treatment of K-ras$^{LSLG12D}$, CAG-LSL-GFP genetically engineered mouse NSCLC model with cisplatin. Data presented as the average number of GFP positive cells per lung±SEM, n=6 mice/group.

In addition, the LSL-K-ras$^{G12D}$ genetically engineered mouse model of NSCLC (Jackson et al., 2001) was crossed to the Z/EG Cre-reporter strain (Novak et al., 2000) and used in this study. Cisplatin (7 mg/kg i.p. every 7 days for 3 doses) was started 12 weeks after AdenoCre infection of the lungs (ie. tumor initiation). Lungs were collected 1 week after the last dose of chemotherapy and tumor cells were isolated by FACS after enzymatic digestion and dissociation. FACS analysis of the of GFP-positive tumor cells present in the lung one week after the final dose of cisplatin revealed a significant decrease in tumor cell number in the cisplatin-treated mice compared to vehicle controls. FIG. 2D (data presented as the average number of GFP positive cells per lung±SEM, n=6/group). Thus, cisplatin treatment of the LSL-K-ras$^{G12D}$ mice resulted in a significant reduction in tumor burden, but it does not result in prolonged survival, indicating that tumors recur after therapy (Oliver et al., 2010).

Although each of the models described above responded to chemotherapy, the tumors relapsed at varying times after therapy, despite the nearly complete cytoreduction. The GFP-labeled cells that survived chemotherapy prior to the onset of tumor re-growth contain the TRICs and were isolated for further study.

Example 3

Enrichment of NRG1 in TRICs

Based on predetermined growth curves for each model, regressed or vehicle treated tumors were collected between 1-3 weeks after the last treatment, but before the onset of regrowth of the chemotherapy treated tumors. Tumor tissue was enzymatically digested and dissociated and GFP positive tumor cells were isolated by fluorescence-activated cell sorting (FACS).

Figure 3A:
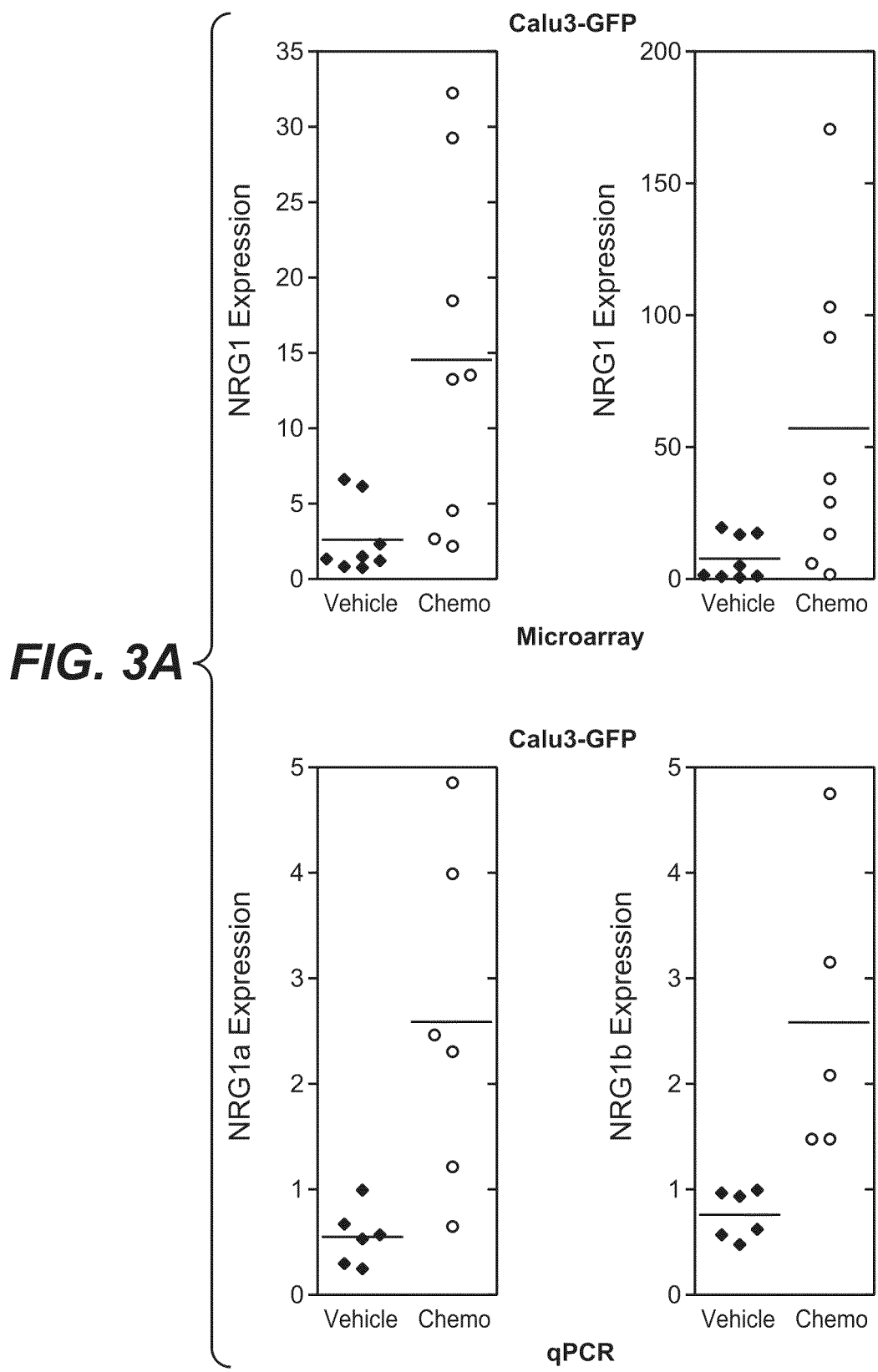
FIG. 3A. Enrichment of NRG1 mRNA in TRICs in the Calu3 xenograft model was demonstrated by two independent probes in a microarray analysis. Enrichment was validated by quantitative real time PCR (qPCR) for NRG1a and NRG1b using RNA isolated from independent tumor samples.

In order to characterize differences in the gene expression profiles of vehicle treated and residual tumor cells, RNA was isolated from the tumor cells (PI$^-$ & GFP$^+$), and expression profiling was performed. Microarray analysis of both the Calu3 and H441 models revealed that NRG1 expression was significantly higher in residual chemo-treated tumor cells compared to vehicle-treated tumor cells (FIG. 3A-B). Enrichment in residual chemo-treated cells was determined using two independent microarray probes. For the Calu3 xenograft model, an 8.6-fold enrichment, (p=0.003, q=0.003) was measured using the first probe (FIG. 3A, left microarray panel) and a 5.3-fold enrichment (p=0.001, q=0.002 (n=8/group)) was measured using the second probe (FIG. 3A, right microarray panel). For the H441 xenograft model, a 4.9-fold enrichment (p<0.001, q=0.009) was determined using the first probe ((FIG. 3B, left microarray panel)) and a 2.8-fold enrichment (p=0.001, q=0.013 (n=8/group)) was determined using the second probe ((FIG. 3B, right microarray panel)).

Due to alternative splicing there are two active isoforms of the NRG1 EGF-like domain that is required for receptor binding, referred to as NRG1 alpha (NRG1α) and NRG1beta (NRGβ). We confirmed the enrichment of NRG1α and NRG1β by quantitative real time PCR (qPCR) (FIG. 3A-B). For the Calu3 xenograft model, NRG1α expression was enriched 4.7-fold (p=0.02) (FIG. 3A, left qPCR panel) and NRG1β was enriched 3.4-fold (p=0.04) (FIG. 3A, right qPCR panel) (n=6/group) using independent tumor samples. For the H441 xenograft model, NRG1α was enriched 11.4-fold (FIG. 3B, left qPCR panel) and NRG1β was enriched 12.1-fold (FIG. 3B, right qPCR panel) using the same tumor samples as the microarray analysis.

Figure 3C:
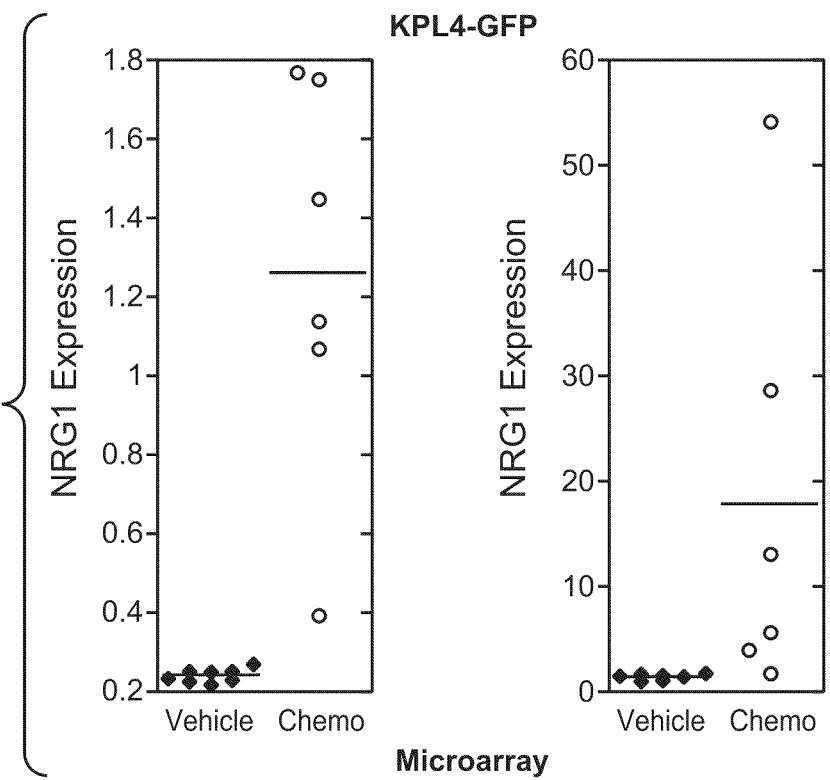
FIG. 3C. Enrichment of NRG1 mRNA in TRICs in the KPL4 breast cancer xenograft model shown by two different microarray probes.

NRG1 mRNA is enriched in TRICs from the KPL4 breast cancer xenograft model. Enrichment was determined using two independent microarray probes (FIG. 3C).

Figure 3D:
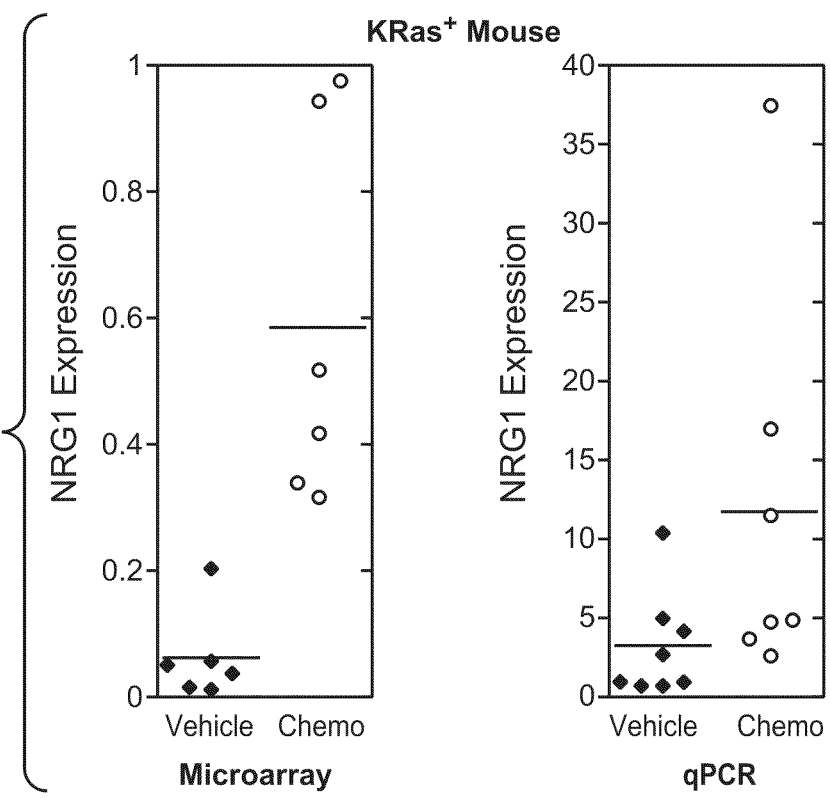
FIG. 3D. Enrichment of NRG1 mRNA in TRICs in the K-ras$^{LSLG}$12D mouse NSCLC model shown by one microarray probe and validated by qPCR.

For the LSL-K-ras$^{G12D}$ model, NRG1 expression was significantly higher in residual chemo-treated tumor cells versus bulk vehicle-treated tumor cells based on microarray. A 13.7-fold enrichment (p<0.001, q=1) (n=6/group) was determined using microarray analysis (FIG. 3D, microarray panel). Enrichment was validated by qPCR on independent samples showing a 9-fold enrichment (p=0.04) (FIG. 3D, qPCR panel).

NRG1 was one of a few genes significantly enriched in the residual treated cells in all 3 models, Calu3, H441 and LSL-K-ras$^{G12D}$). Interestingly, neither HER3 nor HER4 receptor expression was consistently enriched in all models.

The activation of the NRG1 receptor, HER3, was accessed by immunostaining tumors for phospho-HER3. The majority of tumor cells in the residual tumors were p-HER3 positive whereas the vehicle treated tumors showed only scattered clusters of p-HER3 positive cells. Expression of the other HER3 ligand, NRG2, was not found in residual tumor cells. Thus, residual tumor cells express NRG1 and show enhanced receptor activation, demonstrating increased NRG1 autocrine activity.

Example 4

Regulation of NRG1 Expression

Figure 4:
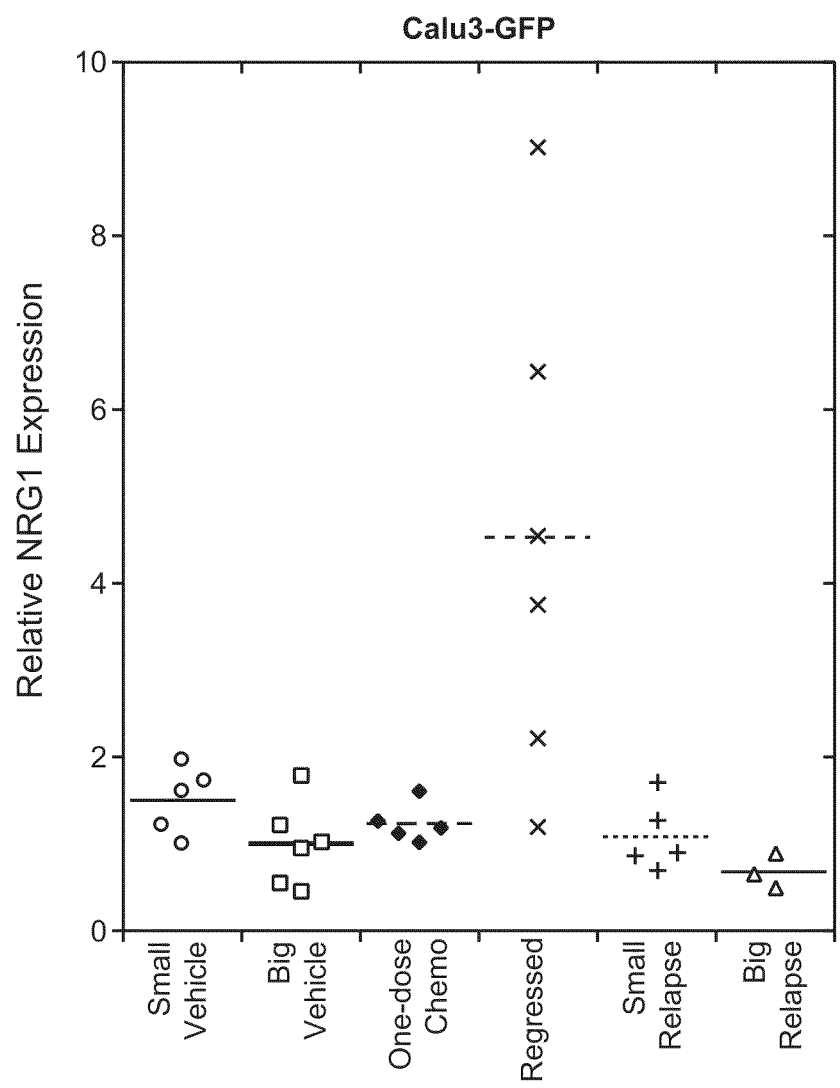
FIG. 4. NRG1 enrichment is specific to residual cells as evidenced by qPCR analysis of tumor cell NRG1 mRNA levels in tumors of various sizes and times after chemotherapy.

The increased expression of NRG1 observed in the residual tumor cells could result from an enrichment of a NRG1-expressing subpopulation of cells present in the primary tumor. Alternatively, chemotherapy might induce NRG1 expression in cells that are then resistant to its cytotoxic effects, or expression levels could be influenced by the tumor size or growth kinetics. To distinguish between these possibilities, NRG1 expression levels was assessed in tumors of different volumes and at various times after chemotherapy by qPCR (FIG. 4). NRG1 mRNA levels did not increase after a single dose of chemotherapy (cisplatin+paclitaxel). In fact, with the exception of the residual tumors, NRG1 levels were equivalent at all of the times and volumes tested. These results demonstrate that NRG1 expression is not induced by chemotherapy or influenced by tumor size, and are consistent with the enrichment of a pre-existing subpopulation of NRG1-expressing cells.

Example 5

Autocrine NRG1-HER Signaling in NSCLC

In order to identify models that co-express both the ligand and its receptors, the expression of NRG1 and its receptors in the parental Calu3 and H441 cells as well as a panel of additional human NSCLC cell lines was examined. Although the expression levels of NRG1α and NRG1β transcripts were heterogeneous among cell lines, they were much higher in the majority of cell lines when compared to normal lung. Surprisingly, in the H441 cells, NRG1 transcript was present only when cells were grown as tumors in vivo. Cultured H441 cells did not express detectable NRG1α or NRG1β transcripts, highlighting the differences in the properties of cells grown in vitro and in vivo. Western analysis of the four HER receptors revealed heterogeneous expression among the 6 human NSCLC lines. Calu3 had the highest level of in vitro expression for all four receptors relative to other cell lines.

To evaluate the possible downstream mediators of NRG1 autocrine signaling, stable sub-lines of Calu3, H441 and H1299 parental cell lines carrying a doxycycline-inducible shRNA (Gray et al., 2007) to NRG1 (shNRG1) and a constitutively expressed dsRED reporter gene were generated. The NRG-1 gene contains multiple promoters and undergoes extensive alternative splicing resulting in at least 15 different isoforms. All active isoforms contain an EGF-like domain that is necessary and sufficient for RTK activation (Holmes et al., 1992; Yarden and Peles, 1991). The shNRG1 was targeted to the common EGF-like domain to enable knockdown of all possible isotypes. Matched stable cell lines with doxycycline-inducible shRNA to Luciferase (shLuc) were generated as controls. There was effective and specific reduction of NRG1α and NRG1β transcripts (~90%) only in the Calu3-shNRG1 cells when cultured in the presence of doxycycline (dox). An associated decrease in p-HER3, p-AKT levels and a slight decrease in p-HER4 in serum-starved Calu3-shNRG1 cells cultured in the presence of dox was measured. There were no detectable changes in the levels of p-Stat3 or p-Mek1/2 in these lysates.

Since H441 cells did not express any NRG1 transcript in vitro, the mediators of NRG1 signaling in these cells were assessed by stimulation with exogenous NRG1 ligand. Upon NRG1 stimulation of serum starved cells, there was an increase in p-HER3 and p-AKT. There were no detectable changes in the levels of p-Stat3 or p-Mek1/2.

NRG1 effector pathways were also evaluated in murine lung cancer cells. Two independent cell lines were derived from LSL-K-ras$^{G12D}$; p53$^{Fl/+}$ lung tumors, LKPH1 and LKPH2 and collectively referred to as LKPH lines (see Example 1). Stable sublines carrying dox-inducible shNrg1 or shLuc were generated. Decreased Nrg1 transcript was seen only in the LKPH shNrg1 cell lines in the presence of dox. Furthermore, there was a decrease in the levels of p-HER3 and p-AKT in serum starved LKPH-shNRG1 cells cultured in the presence of dox. Changes in the levels of p-Mek1/2 and p-Stat3 in cultures lacking Nrg1 mRNA were not detectable by western blot, suggesting that these effector pathways were not engaged by Nrg1.

Together, the data from NRG1 stimulation of H441 cells and NRG1 knockdown in Calu3 and LKPH1/2 cells suggest that the PI3K pathway is the major downstream effector of NRG1 signaling in NSCLC cells. Increased expression of NRG1 transcripts and HER receptors in both human and mouse NSCLC models and decreased activity of HER3 signaling in cultured tumor cells upon NRG1 knockdown suggest that there is an autocrine NRG1-HER3 signaling loop in NSCLC. In addition, its increased expression in residual tumor cells (FIG. 3) suggests that NRG1 autocrine signaling may play a role in chemoresistance and/or disease relapse.

Example 6

NRG1 Knockdown Delays Tumor Relapse after Chemotherapy

The effects of NRG1 knockdown on primary tumor growth and relapse after chemotherapy was determined by evaluating effects of NRG1 knockdown alone or in combination with chemotherapy. Three human NSCLC models that exhibit varying expression patterns of the HER family receptors were used in this study. The Calu3 model has high protein levels of all the receptors, H441 shows strong expression of HER2 and HER3 and moderate HER1, and H1299 shows moderate levels HER1, 2 and 3.

Figure 5A:
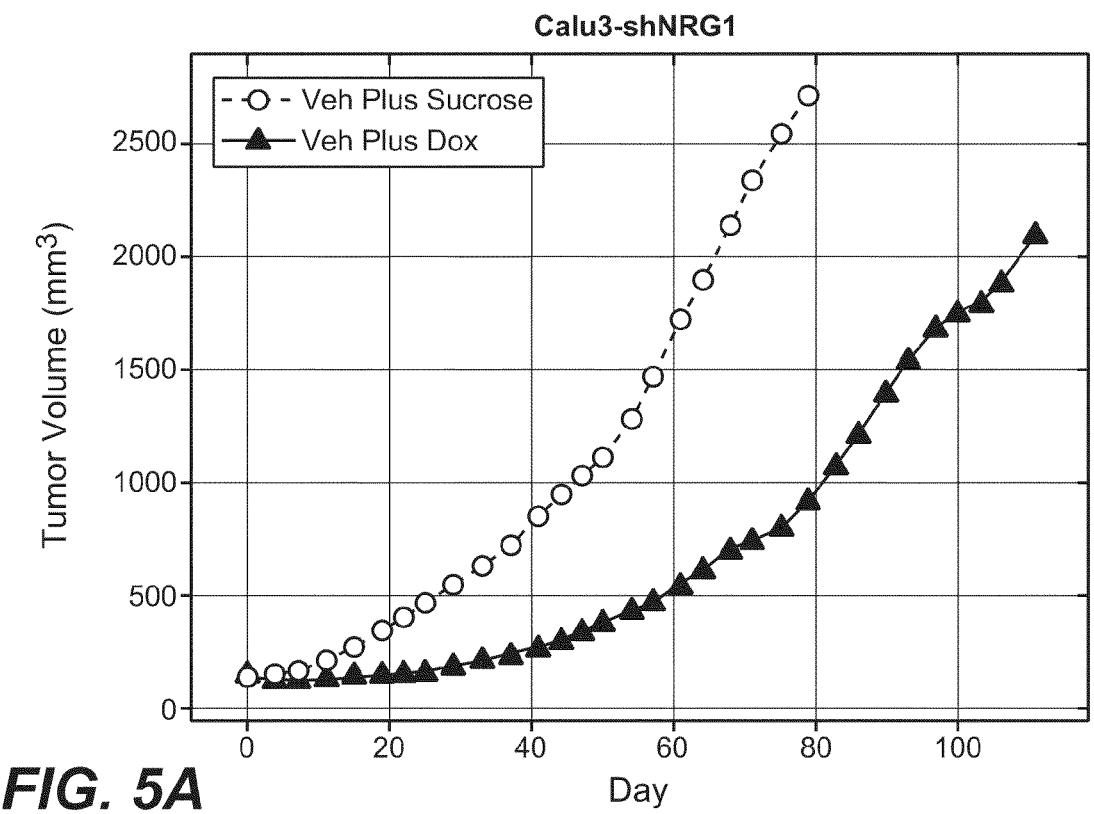
FIG. 5A. Graph showing tumor growth curves for mice with established Calu3-shNRG1 xenograft tumors administered vehicle (sucrose) or dox (2 gm/L) in their drinking water ad libitum. Tumor volume was measured twice a week for the duration of the study. Data presented as Linear Mixed Effect (LME) model generated fit of tumor volume graphed as cubic splines with auto-determined knots.

To determine the efficacy of NRG1-targeting in the Calu3 model, Calu3-shNRG1 tumor bearing mice were assigned to four groups; 1) vehicle+sucrose, 2) vehicle+dox, 3) chemotherapy+sucrose, and 4) chemotherapy+dox. The same chemotherapeutic regimens as described above in Example 2 were used and 5% sucrose or dox (2 g/L) was administered orally in the drinking water ad libitum. Tumor volume was measured twice a week for the duration of the study. Tumor Growth curves were generated for the individual mice used in the study (n=12 mice for vehicle+sucrose and n=13 mice for vehicle+dox) and are presented as Linear Mixed Effect (LME) model generated fit of tumor volume graphed as cubic splines with auto-determined knots in FIGS. 5A and 5B. There was a significant delay in tumor volume doubling time in the vehicle+dox group (time to doubling (TDT)= 44.5 days) vs. vehicle+sucrose (TDT=17 days), suggesting that NRG1 knockdown partially inhibits tumor growth (FIG. 5A).

Figure 5B:
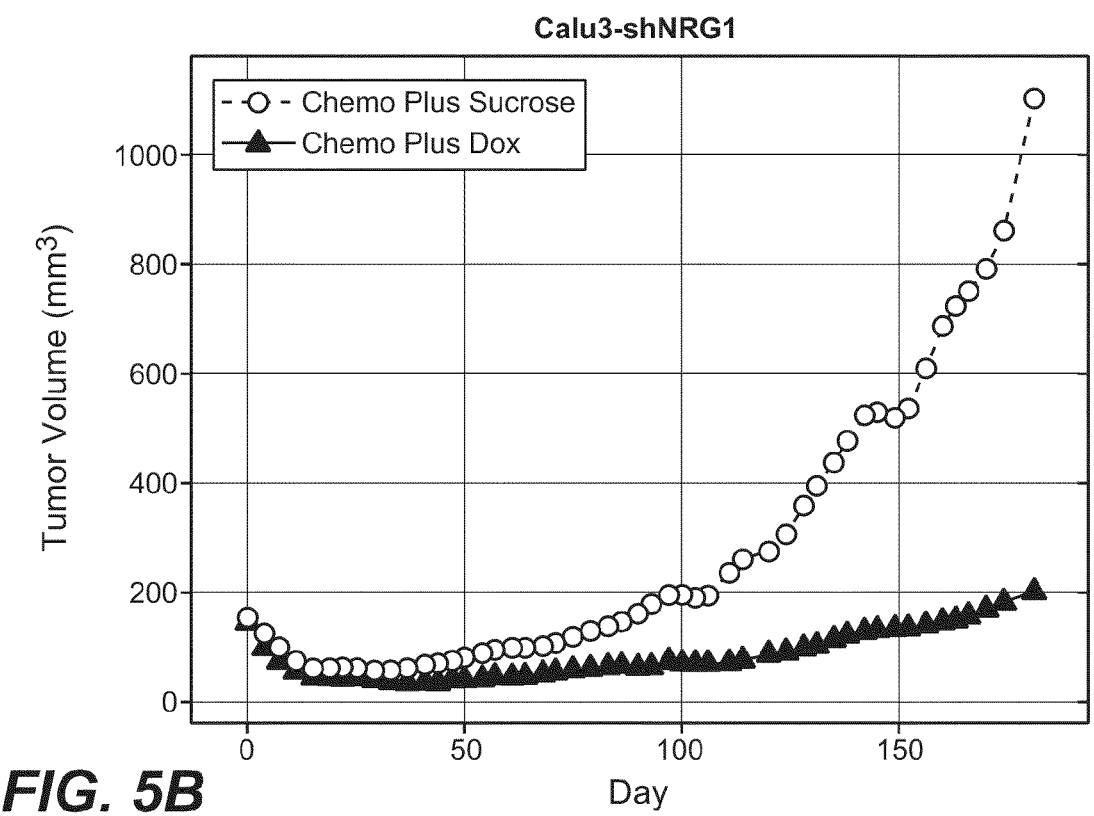
FIG. 5B. Graph showing tumor growth curves for mice with established Calu3-shNRG1 xenograft tumors treated with chemo+sucrose or chemo+dox. Data presented as LME model generated fit of tumor volume graphed as cubic splines with auto-determined knots.

The effect of NRG1 on tumor relapse was assessed by comparing the growth of tumors in the chemotherapy+ sucrose with those in the chemotherapy+dox group. There was significant delay in tumor relapse in the chemotherapy+ dox group (TDT>181 days, not reached by end of study) vs. chemotherapy+sucrose (TDT=124 days) (FIG. 5B). Furthermore, many of the relapsed tumors from the dox-treated mice, both with and without chemotherapy, were composed primarily of a brownish/black mucus-like liquid with only a small region of viable tumor tissue. Therefore, the measured volumes were considerably larger than the actual tumor volume in the dox-treated groups. No differences were observed between any of the groups in the Calu3-shLuc control study. In addition, immunohistochemistry (IHC) was performed for the proliferation marker Ki67 on the Calu3 tumors 3 days after the last dose of chemotherapy. There was a markedly lower proportion of Ki67 positive cells in the chemotherapy+dox treated tumors compared to the chemotherapy+sucrose tumors, suggesting that NRG1 signaling stimulates proliferation in residual tumor cells after chemotherapy.

The mRNA levels of NRG1α and NRG1β isoforms in tumor cells collected at early and late time points was determined NRG1 transcripts increased at the late timepoint indicating that knockdown is not maintained in vivo.

Figure 6A:
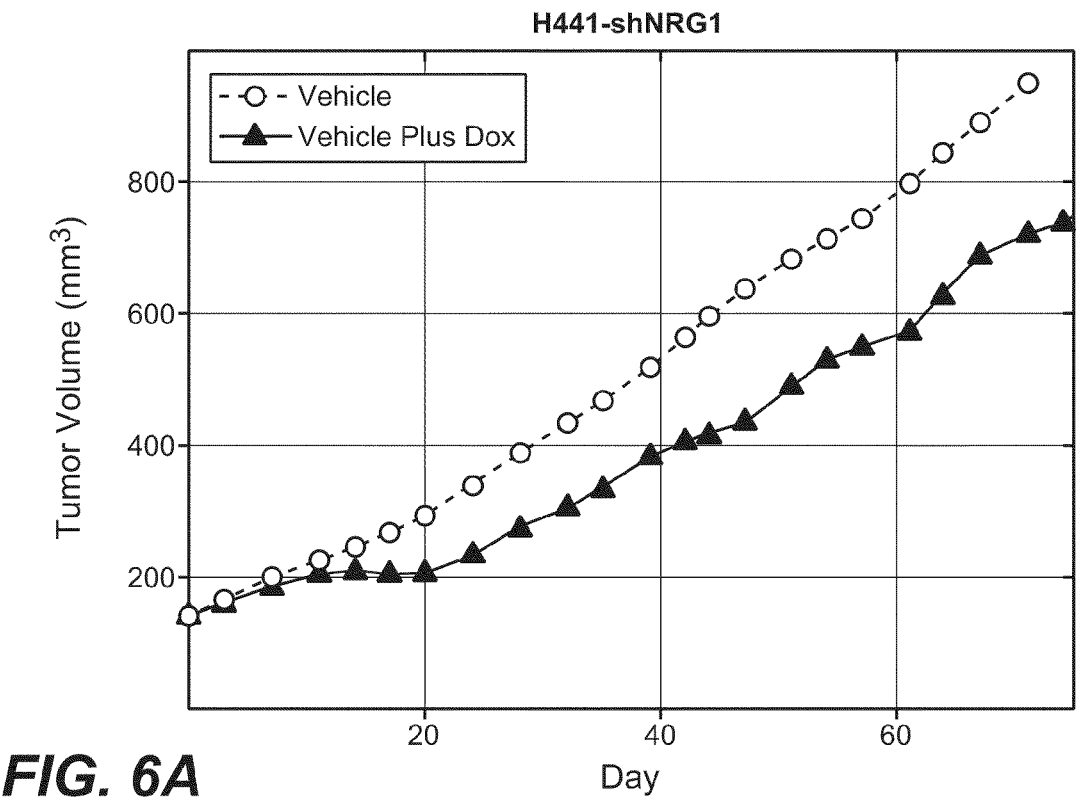
FIG. 6A. Graph showing tumor growth curves for mice with established H441-shNRG1 xenograft tumors treated with sucrose or dox (n=12/group). Data is presented as LME fit analysis of tumor volume graphed as cubic splines with auto-determined knots.
Figure 6B:
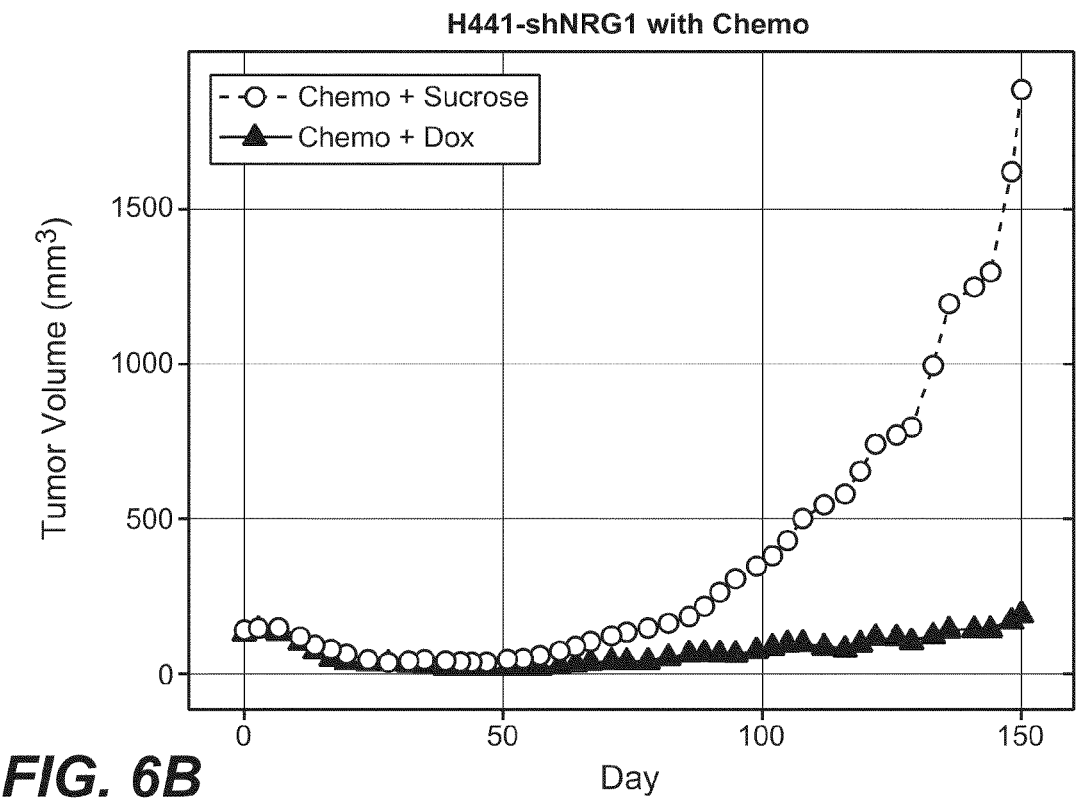
FIG. 6B. Graph showing tumor growth curves for mice with established H441-shNRG1 xenograft tumors treated with chemo+sucrose or chemo+dox (n=12/group). Data presented as LME fit analysis of tumor volume graphed as cubic splines with auto-determined knots.

The effect of NRG1 knockdown in the H441 xenograft model was also examined. Although there was a minimal effect on primary tumor growth (FIG. 6A (n=12/group) tumor growth curves presented as LME fit analysis of tumor volume graphed as cubic splines with auto-determined knots), there was a significant delay in tumor relapse in the chemotherapy+dox group (TDT>150 days, not reached by end of study) vs. chemotherapy+sucrose (TDT=94 days) (FIG. 6B ((n=12/group)). There was no such difference in tumor volume in the H441-shLuc in vivo study. Similar to the Calu3 xenograft model, the H441 model also exhibited increased levels of NRG1 transcripts at the late time point.

To investigate the mechanism behind the restoration of NRG1 levels the tumor cells were analyzed for expression of the lentivirally transduced genes. Because the lentivirus used to transduce the cells with the shRNA also includes a dsRed marker gene, the proportion of dsRED positive tumor cells at early and late time points were compared by flow cytometry. In vivo loss of lentiviral gene expression was assessed for tumors at early (5 days) and late time points (>100 days) by FACS analysis examining the proportion of tumor cells (human specific-ESA positive) that express the lentiviral dsRed transgene. Mice in the early time point received sucrose or dox and mice in the late timepoint received chemo+sucrose or chemo+dox. A significant reduction in the proportion of dsRed positive cells at the late time point for both sucrose and dox treated tumors was observed, with the reduction being significantly greater for the dox treated tumors (1.8-fold vs. 4.1-fold, p=0.007). This suggests that loss of viral transgene expression correlates with a restoration of NRG1 levels.

Figure 7A:
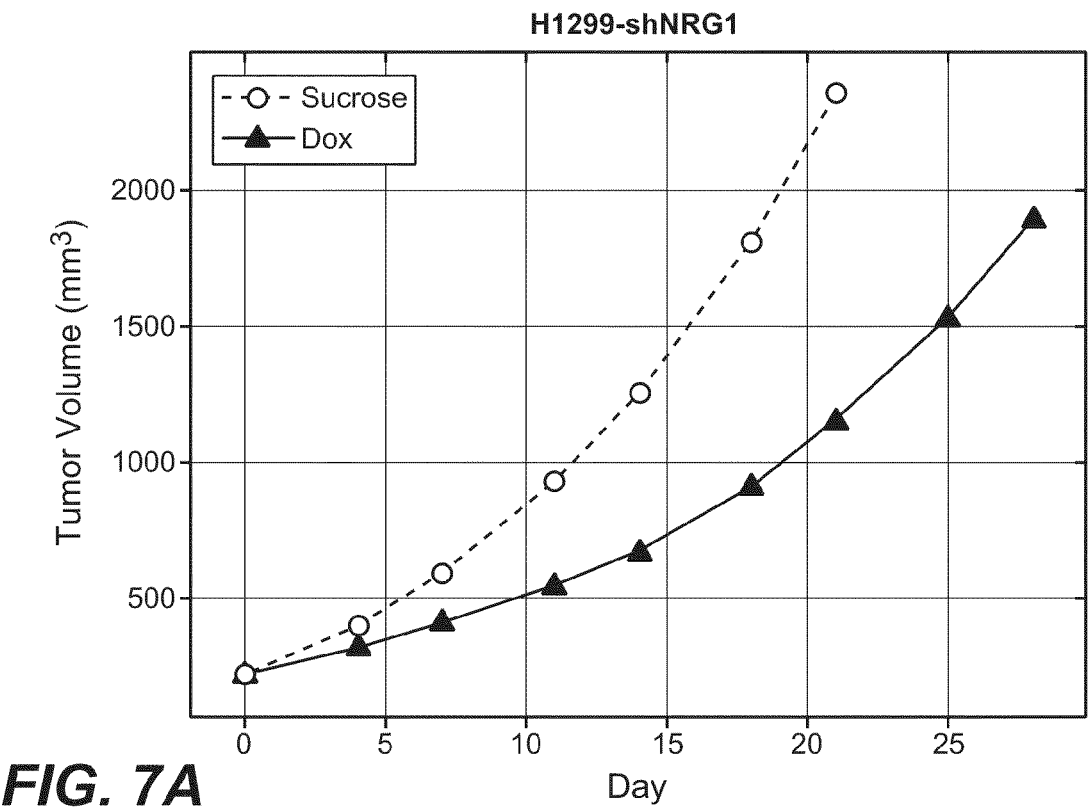
FIG. 7A. Graph showing tumor growth curves for mice with established H1299-shNRG1 xenograft tumors treated with sucrose or dox (n=12 mice/group). Data is presented as LME fit analysis of tumor volume graphed as cubic splines with auto-determined knots.
Figure 7B:
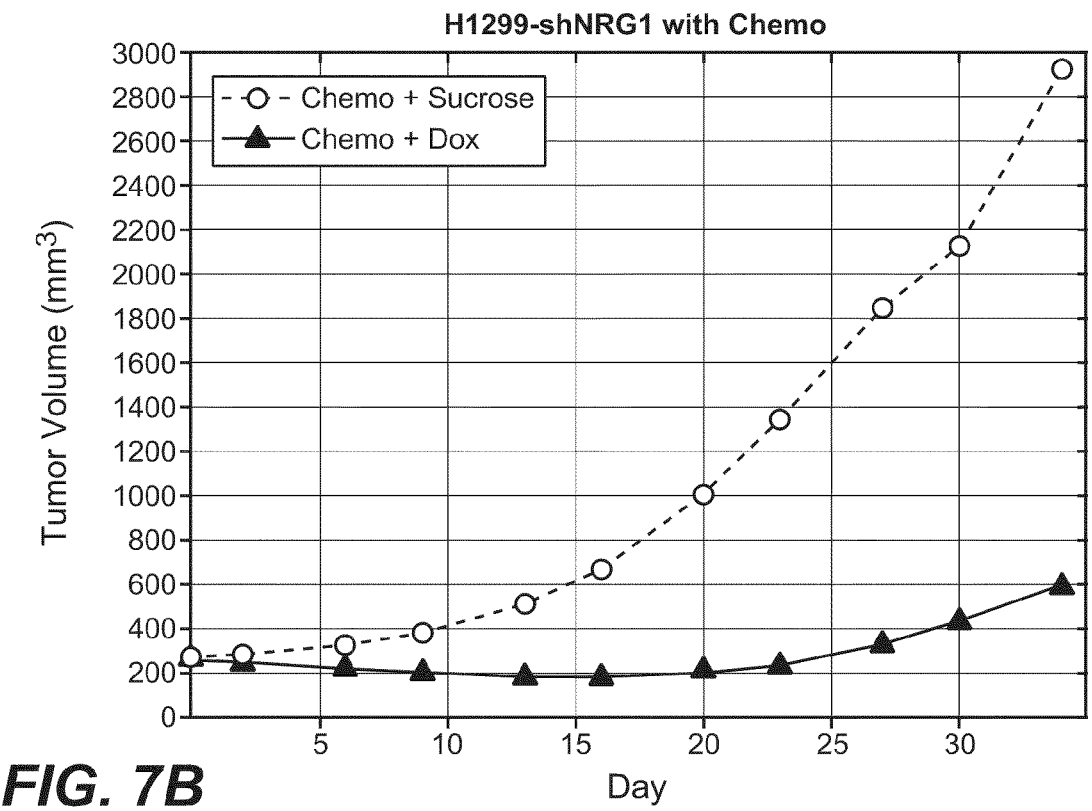
FIG. 7B. Graph showing tumor growth curves for mice with established H1299-shNRG1 xenograft tumors treated with chemo+sucrose or chemo+dox (n=12/group). Data is presented as LME fit analysis of tumor volume graphed as cubic splines with auto-determined knots.

Both Calu3 and H441 cells show increased levels of HER3 protein, raising the question of whether the role of NRG1 in tumor relapse is specific to tumors with receptor overexpression. To address this question the H1299 xenograft model that has much lower levels of HER3 was used. Knockdown of NRG1 alone had only a modest effect on primary tumor growth, similar to the H441 model. In contrast and despite the very aggressive growth of the H1299 tumors, NRG1 knockdown led to an enhanced response to chemotherapy resulting and a significant delay in tumor relapse in the chemotherapy+dox group (TDT=30.45 days) vs. chemotherapy+sucrose (TDT=11.5 days) (n=12/group) (FIGS. 7A, B).

Furthermore, a stable subline of H1299 expressing a different shRNA to NRG1 (shNRG1.2) was generated that resulted in a more modest reduction in NRG1 mRNA levels. In vivo studies with H1299-shNRG1.2 also demonstrated an enhanced response to chemotherapy upon NRG1 knockdown. However, the magnitude of the growth inhibition was smaller in this model, consistent with the lesser degree of NRG1 knockdown. There was no difference in tumor volumes between sucrose and dox treated groups with or without chemotherapy in H1299-shLuc in vivo studies.

Inhibition of NRG1 autocrine signaling by shRNA mediated knockdown had only modest to moderate effects on primary tumor growth but dramatically delayed tumor relapse after chemotherapy. Despite the inability to maintain long-term knockdown of NRG1 in the xenograft models, we observed a significant delay in tumor relapse upon NRG1 knockdown. These findings suggest there are differences in the key pathways regulating primary tumor growth, and chemoresistance and relapse.

Example 7

Inhibition of NRG1 Signaling Using a Ligand Trap Delays Tumor Relapse

To test the role of NRG1 signaling in promoting relapse after chemotherapy in the LSL-K-ras$^{G12D}$; p53$^{Fl/+}$ mouse model, a ligand-trap approach to sequester NRG1 and prevent its binding to receptors in vivo was employed. A fusion of the human HER4 extracellular domain (HER4-ECD) fused to murine IgG2A Fc was generated. HER4 shows high affinity binding for NRG1 (Tzahar et al., 1994). When HER4-ECD was added to serum starved LKPH1 and LKPH2 cells in vitro, inhibition of NRG1/HER3 signaling was observed as demonstrated by diminished p-HER3 levels. Thus, in vitro the molecule behaved as expected in interfering with autocrine-mediated NRG1 signaling.

Figure 8A:
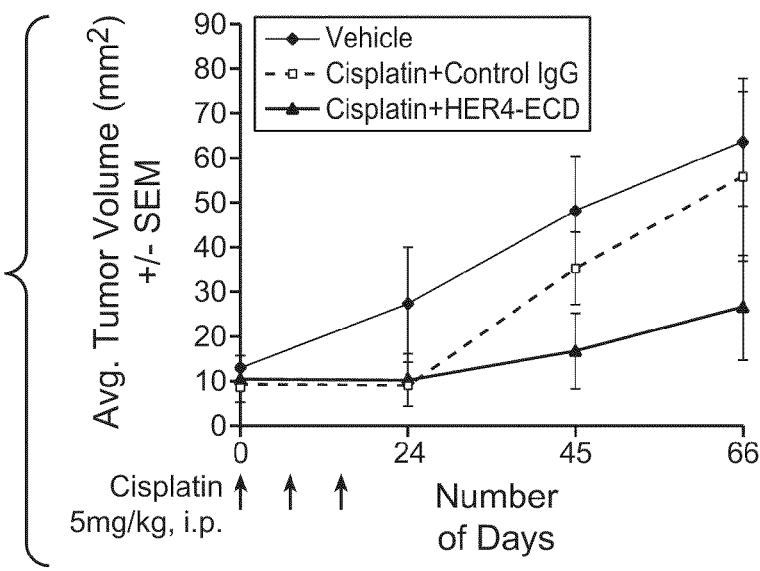
FIG. 8A. Graph showing average tumor volume+/−SEM for LSL-K-ras$^{G12D}$; p53$^{Fl/+}$ mice treated with vehicle+control IgG (n=6), cisplatin+control IgG (n=6), or cisplatin+HER4ECD-Fc (n=8). Ragweed, control murine IgG2a antibody.
Figure 8B:
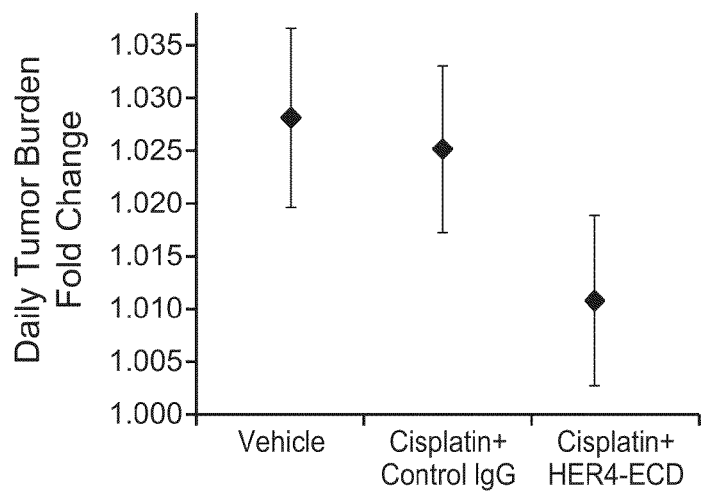
FIG. 8B. Graph showing the daily fold change in tumor burden by treatment regimen with 95% confidence intervals.

Lung tumor bearing LSL-K-ras$^{G12D}$; p53$^{Fl/+}$ mice were imaged by X-ray micro-computed tomography (micro-CT) at the start of the study (day 0), segregated into three groups of equal starting tumor burdens and treated as follows: 1) PBS+control IgG2A; 2) cisplatin+control IgG2A; and 3) cisplatin+HER4-ECD. Mice underwent longitudinal micro-CT scans to measure changes in tumor burden. Analysis of average tumor burden (FIG. 8A (graph represents average tumor volume+/−SEM, ragweed, control murine IgG2a antibody)) and tumor growth rate ((FIG. 8B (graph showing daily fold change in tumor burden by treatment regimen with 95% confidence intervals)) revealed that only the combination of cisplatin+HER4-ECD but not cisplatin alone resulted in a significant inhibition of tumor growth. Although the cisplatin treated mice showed stasis of their tumor growth at the first micro-CT scan after chemotherapy, the average tumor burden at the conclusion of the study and overall tumor growth rate were not significantly different between the vehicle and cisplatin treated groups (FIG. 8A-B).

Figure 8C:
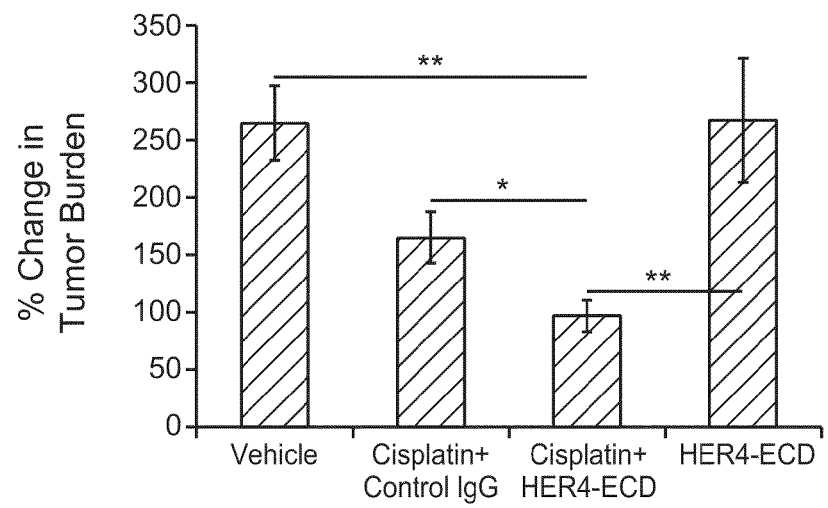
FIG. 8C. Graph showing average percent change in tumor burden from baseline±SEM for LSL-K-ras$^{G12D}$; p53$^{Fl/Fl}$ mice treated with vehicle+control IgG (n=10), cisplatin+control IgG (n=11), cisplatin+HER4-ECD (n=8) or Vehicle+HER4-ECD (n=7).

A second study was carried out in LSL-K-ras$^{G12D}$; p53$^{Fl/Fl}$ mice as described above. However, this study included a HER4-ECD single agent arm in addition to the groups described above. Analysis of tumor burden by micro-CT on day 28 revealed a significant reduction in tumor burden in the cisplatin+HER4-ECD treated mice compared to cisplatin+vehicle treated mice and all other groups (FIG. 8C). In contrast, there was no effect of HER4-ECD treatment alone on tumor growth, further supporting a unique role for NRG1 autocrine signaling in chemoresistance and/or tumor regrowth. In this study, LSL-K-ras$^{G12D}$; p53$^{Fl/Fl}$ mice were treated with vehicle+control IgG (n=10), cisplatin+control IgG (n=11), cisplatin+HER4-ECD (n=8) or Vehicle+HER4-ECD (n=7). The graph in FIG. 8C represents average percent change in tumor burden from baseline±SEM. Dunnett's Multiple Comparison Test was utilized to compare all of the treatment groups against the vehicle control ** p=0.0016. Combination activity was assessed using an unpaired t-test against its monotherapy * p<0.05, ** p<0.01.

Example 8

NRG1 Receptor Usage in NSCLC

To understand which HER receptors are employed in NRG1 autocrine signaling in NSCLC, we evaluated the effects of HER3 and HER4 knockdown on tumor cell proliferation. The Calu3 NSCLC model expressed high levels of all the HER family receptors compared to other cell lines. Stable dox-inducible shHER3 (Calu3-shHER3) and shHER4 (Calu3-shHER4) Calu3 cell sub-lines were generated, as well as a control cell line carrying a dox-inducible shRNA to Luciferase. HER3 and HER4 transcript levels were decreased in Calu3-shHER3 and Calu3-shHER4 respectively in the presence of dox (2 ug/ml) as measured by qPCR, resulting in decreased protein levels, as measured by Western blot. Interestingly, the extent of p-AKT downregulation observed in Calu3-shHER3 in the presence of dox was much greater that seen in Calu3-shHER4, suggesting that HER3 is the predominant receptor mediating NRG1 autocrine signaling in the Calu3 model.

To confirm this role in vivo, studies using Calu3-shHER3 and Calu3-shHER4 xenograft models treated with either sucrose or dox were performed. Mice with established Calu3-shHER3 or Calu3-shHer4 xenograft tumors were administered vehicle (sucrose) or dox (2 gm/L) in their drinking water ad libitum (n=14/group). There was substantial inhibition of Calu3-shHER3 tumor growth in the mice receiving dox treatment (TDT=19 days) compared to those receiving sucrose treatment (TDT=11 days). However, there was not a notable inhibition of tumor growth in the Calu3-shHER4 in vivo study.

The in vitro receptor analysis and in vivo studies indicate that despite high HER4 levels, NRG1 autocrine signaling occurs mainly through HER3 in this model.

NRG1 autocrine signaling was assessed in the H522 human NSCLC cell line, which expresses high levels of HER4 but no detectable HER3. A H522-shNRG1 subline was generated. Administration of dox to serum starved H522-shNRG1 cells results in decreased levels of phospho-HER4 and phospho-S6. No differences were observed in H522-shLuc control cells siRNA-mediated knockdown was used to test the requirement for each HER family member in cell proliferation. Only knockdown of HER4 and not the other HER family receptors resulted in decreased cell proliferation. These data suggest that NRG1 autocrine signaling occurs through HER4 in H522 cells. Thus, NRG1 autocrine signaling in NSCLC can be mediated by both HER3 and HER4.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

REFERENCES

1) Lung Cancer Principles and Practice, Third edn (2005) (Philadelphia: Lippincott Williams & Wilkins).
2) Agus, D. B., et al. (2002). Targeting ligand-activated ErbB2 signaling inhibits breast and prostate tumor growth. Cancer cell 2, 127-137.
3) al Moustafa, A. E., et al (1999). Expression of P185erbB-2, P160erbB-3, P180erbB-4, and heregulin alpha in human normal bronchial epithelial and lung cancer cell lines. Anticancer Res 19, 481-486.
4) Baldi, P., and Long, A. D. (2001). A Bayesian framework for the analysis of microarray expression data: regularized t-test and statistical inferences of gene changes. Bioinformatics 17, 509-519.
5) Bao, S., et al. (2006). Stem cell-like glioma cells promote tumor angiogenesis through vascular endothelial growth factor. Cancer research 66, 7843-7848.
6) Brennan, S. K., and Matsui, W. (2009). Cancer stem cells: controversies in multiple myeloma. Journal of molecular medicine (Berlin, Germany) 87, 1079-1085.
7) Carey, K. D., et al. (2006). Kinetic analysis of epidermal growth factor receptor somatic mutant proteins shows increased sensitivity to the epidermal growth factor receptor tyrosine kinase inhibitor, erlotinib. Cancer research 66, 8163-8171.
8) Costello, R. T., et al. (2000). Human acute myeloid leukemia CD34+/CD38− progenitor cells have decreased sensitivity to chemotherapy and Fas-induced apoptosis, reduced immunogenicity, and impaired dendritic cell transformation capacities. Cancer research 60, 4403-4411.
9) Dahabreh, I. J., et al. (2010). Somatic EGFR mutation and gene copy gain as predictive biomarkers for response to tyrosine kinase inhibitors in non-small cell lung cancer. Clin Cancer Res 16, 291-303.
10) Dean, M., Fojo, T., and Bates, S. (2005). Tumour stem cells and drug resistance. Nature reviews 5, 275-284.
11) Ding, L., et al. (2008). Somatic mutations affect key pathways in lung adenocarcinoma. Nature 455, 1069-1075.
12) Doebele, R. C., et al. (2010). New strategies to overcome limitations of reversible EGFR tyrosine kinase inhibitor therapy in non-small cell lung cancer. Lung Cancer 69, 1-12.
13) Dylla, S. J., et al. (2008). Colorectal cancer stem cells are enriched in xenogeneic tumors following chemotherapy. PloS one 3, e2428.
14) Goffin, J., et al. (2010). First-line systemic chemotherapy in the treatment of advanced non-small cell lung cancer: a systematic review. J Thorac Oncol 5, 260-274.
15) Gollamudi, M., et al. (2004). Autocrine activation of ErbB2/ErbB3 receptor complex by NRG-1 in non-small cell lung cancer cell lines. Lung Cancer 43, 135-143.
16) Gray, D. C., et al. (2007). pHUSH: a single vector system for conditional gene expression. BMC Biotechnol 7, 61.
17) Hirsch, F. R., et al. (2007). Combination of EGFR gene copy number and protein expression predicts outcome for advanced non-small-cell lung cancer patients treated with gefitinib. Ann Oncol 18, 752-760.
18) Holmes, W. E., et al. (1992). Identification of heregulin, a specific activator of p185erbB2. Science (New York, N.Y. 256, 1205-1210.
19) Horner M J, et al (eds) SEER Cancer Statistics Review, 1975-2006. In, (National Cancer Institute. Bethesda, Md.).
20) Jackson, E. L., et al. (2001). Analysis of lung tumor initiation and progression using conditional expression of oncogenic K-ras. Genes Dev 15, 3243-3248.
21) Johnson, B. E., and Janne, P. A. (2006). Rationale for a phase II trial of pertuzumab, a HER-2 dimerization inhibitor, in patients with non-small cell lung cancer. Clin Cancer Res 12, 4436s-4440s.
22) Junttila, T. T., et al. (2009). Ligand-independent HER2/HER3/PI3K complex is disrupted by trastuzumab and is effectively inhibited by the PI3K inhibitor GDC-0941. Cancer cell 15, 429-440.
23) Kosaka, T., et al. (2004). Mutations of the epidermal growth factor receptor gene in lung cancer: biological and clinical implications. Cancer research 64, 8919-8923.
24) Kuyama, S., et al. (2008). Impact of HER2 gene and protein status on the treatment outcome of cisplatin-based chemoradiotherapy for locally advanced non-small cell lung cancer. J Thorac Oncol 3, 477-482.
25) Li, Q., et al. (2004). Development of an autocrine neuregulin signaling loop with malignant transformation of human breast epithelial cells. Cancer research 64, 7078-7085.
26) Liu, L. Z., et al. (2007). AKT1 amplification regulates cisplatin resistance in human lung cancer cells through the mammalian target of rapamycin/p70S6K1 pathway. Cancer research 67, 6325-6332.
27) Lynch, T. J., et al. (2004). Activating mutations in the epidermal growth factor receptor underlying responsiveness of non-small-cell lung cancer to gefitinib. N Engl J Med 350, 2129-2139.
28) Marchetti, A., et al. (2005). EGFR mutations in non-small-cell lung cancer: analysis of a large series of cases and development of a rapid and sensitive method for diagnostic screening with potential implications on pharmacologic treatment. J Clin Oncol 23, 857-865.
29) Matsui, W., et al. (2004). Characterization of clonogenic multiple myeloma cells. Blood 103, 2332-2336.
30) Novak, A., et al. Z/EG, a double reporter mouse line that expresses enhanced green fluorescent protein upon Cre-mediated excision. Genesis 28, 147-155.
31) Oliver, T. G., et al. (2010). Chronic cisplatin treatment promotes enhanced damage repair and tumor progression in a mouse model of lung cancer. Genes Dev 24, 837-852.
32) Paez, J. G., et al. (2004). EGFR mutations in lung cancer: correlation with clinical response to gefitinib therapy. Science (New York, N.Y. 304, 1497-1500.

33) Pao, W., et al (2005). Acquired resistance of lung adenocarcinomas to gefitinib or erlotinib is associated with a second mutation in the EGFR kinase domain. PLoS Med 2, e73.
34) Patel, N. V., et al. (2000). Neuregulin-1 and human epidermal growth factor receptors 2 and 3 play a role in human lung development in vitro. American journal of respiratory cell and molecular biology 22, 432-440.
35) Phillips, T. M., et al. (2006). The response of CD24 (-/low)/CD44+ breast cancer-initiating cells to radiation. Journal of the National Cancer Institute 98, 1777-1785.
36) Reissmann, P. T., et al. (1999). Amplification and overexpression of the cyclin D1 and epidermal growth factor receptor genes in non-small-cell lung cancer. Lung Cancer Study Group. J Cancer Res Clin Oncol 125, 61-70.
37) Schaefer, G., et al. (1997). Gamma-heregulin: a novel heregulin isoform that is an autocrine growth factor for the human breast cancer cell line, MDA-MB-175. Oncogene 15, 1385-1394.
38) Sheng, Q., et al. (2010). An Activated ErbB3/NRG1 Autocrine Loop Supports In Vivo Proliferation in Ovarian Cancer Cells. Cancer cell 17, 298-310.
39) Shi, D., et al. (1992). Overexpression of the c-erbB-2/neu-encoded p185 protein in primary lung cancer. Mol Carcinog 5, 213-218.
40) Shigematsu, H., Lin, L., et al. (2005). Clinical and biological features associated with epidermal growth factor receptor gene mutations in lung cancers. Journal of the National Cancer Institute 97, 339-346.
41) Singh, M., Lima, et al. (2010). Assessing therapeutic responses in Kras mutant cancers using genetically engineered mouse models. Nat Biotechnol 28, 585-593.
42) Sinnberg, T., et al. (2009) Inhibition of PI3K-AKT-mTOR signaling sensitizes melanoma cells to cisplatin and temozolomide. J Invest Dermatol 129, 1500-1515.
43) Storey, J. D., and Tibshirani, R. (2003). Statistical significance for genomewide studies. Proceedings of the National Academy of Sciences of the United States of America 100, 9440-9445.
44) Tzahar, E., et al. (1994). ErbB-3 and ErbB-4 function as the respective low and high affinity receptors of all Neu differentiation factor/heregulin isoforms. J Biol Chem 269, 25226-25233.
45) Weiner, D. B., et al. (1990). Expression of the neu gene-encoded protein (P185neu) in human non-small cell lung carcinomas of the lung. Cancer research 50, 421-425.
46) Yarden, Y., and Peles, E. (1991). Biochemical analysis of the ligand for the neu oncogenic receptor. Biochemistry 30, 3543-3550.
47) Yuste, L., et al. (2005). Activation of ErbB2 by overexpression or by transmembrane neuregulin results in differential signaling and sensitivity to herceptin. Cancer research 65, 6801-6810.
48) Zhou, B. B., et al. (2006). Targeting ADAM-mediated ligand cleavage to inhibit HER3 and EGFR pathways in non-small cell lung cancer. Cancer cell 10, 39-50.

What is claimed is:

1. A method of increasing time to tumor recurrence in a cancer patient whose cancer was previously treated comprising administering to the patient an effective amount of a neuregulin antagonist and a chemotherapeutic, wherein the neuregulin antagonist is an anti-NRG1 antibody and wherein the chemotherapeutic agent is selected from the group consisting of paclitaxel, cisplatin, and a combination of paclitaxel and cisplatin and further wherein the cancer is selected from the group consisting of non-small cell lung cancer, breast cancer, ovarian cancer, head and neck cancer, cervical cancer, bladder cancer , oesophageal cancer, prostate cancer, and colorectal cancer.

2. The method of claim 1, wherein the increase in time to tumor recurrence is at least 1.25 fold greater than the time to recurrence in the absence of the neuregulin antagonist.

3. The method of claim 1, wherein the increase in time to tumor recurrence is at least 1.50 fold greater than the time to recurrence in the absence of the neuregulin antagonist.

4. The method of claim 1, wherein the chemotherapeutic agent is paclitaxel.

5. The method of claim 1, wherein the chemotherapeutic agent is cisplatin.

6. The method of claim 1, wherein the chemotherapeutic agent is a combination of paclitaxel and cisplatin.

7. The method of claim 1, wherein the cancer is non-small cell lung cancer.

8. The method of claim 1, wherein the cancer is breast cancer.

9. The method of claim 1, wherein the cancer is ovarian cancer.

10. The method of claim 1, wherein the cancer is head and neck cancer.

11. The method of claim 1, wherein the cancer is cervical cancer.

12. The method of claim 1, wherein the cancer is bladder cancer.

13. The method of claim 1, wherein the cancer oesophageal cancer.

14. The method of claim 1, wherein the cancer is prostate cancer.

15. The method of claim 1, wherein the cancer is colorectal cancer.

* * * * *